US009799231B2

(12) United States Patent
Tavori et al.

(10) Patent No.: US 9,799,231 B2
(45) Date of Patent: Oct. 24, 2017

(54) APPARATUS AND METHODS FOR CORRECTIVE GUIDANCE OF EATING BEHAVIOR

(75) Inventors: Isaac Tavori, Hertzeliya (IL); Lorentz Lior Fleischer, Tel Aviv (IL); Erez Hochman, Hertzeliya (IL)

(73) Assignees: Isaac Tavori, Hertzeliya (IL); Lorentz Lior Fleischer, Tel-Aviv (IL)

( * ) Notice: Subject to any disclaimer, the term of this patent is extended or adjusted under 35 U.S.C. 154(b) by 771 days.

(21) Appl. No.: 14/125,725

(22) PCT Filed: Jun. 13, 2012

(86) PCT No.: PCT/IL2012/000231
§ 371 (c)(1),
(2), (4) Date: Jan. 9, 2014

(87) PCT Pub. No.: WO2012/172542
PCT Pub. Date: Dec. 20, 2012

(65) Prior Publication Data
US 2014/0127652 A1  May 8, 2014

Related U.S. Application Data

(60) Provisional application No. 61/496,099, filed on Jun. 13, 2011.

(51) Int. Cl.
*A61F 2/02* (2006.01)
*G09B 19/00* (2006.01)
*A61F 5/00* (2006.01)

(52) U.S. Cl.
CPC .......... *G09B 19/0092* (2013.01); *A61F 5/003* (2013.01); *A61F 5/005* (2013.01);
(Continued)

(58) Field of Classification Search
CPC ....................................................... A61F 5/005
See application file for complete search history.

(56) References Cited

U.S. PATENT DOCUMENTS

2006/0173238 A1  8/2006  Starkebaum
2007/0156013 A1  7/2007  Birk
(Continued)

FOREIGN PATENT DOCUMENTS

WO  2009050709  4/2009

OTHER PUBLICATIONS

Guidance for the Use of Bayesian Statistics in Medical Device Clinical Trials: Center for Biologics Evaluation and Research; Feb. 5, 2010; pp. 1-50.
(Continued)

*Primary Examiner* — Charles A Marmor, II
*Assistant Examiner* — Shannon McBride
(74) *Attorney, Agent, or Firm* — Troutman Sanders LLP

(57) ABSTRACT

A method for modifying the eating behavior of a patient equipped with a gastric restriction apparatus includes the steps of: a. providing an adjustable gastric band (AGB); b. providing a pressure sensor to measure pressure within the AGB; c. providing a processing unit containing instructions to collect a set of pressure measurement and to analyze the set pressure measurement; d. providing a data base comprising data concerning pressure exerted within the AGB by a bolus of liquid food, a bolus of semiliquid food, and a bolus of solid food; e. recording the sets of pressure measurements; f. recording the results; g. communicating the results; h. placing the AGB in position; i. measuring the pressure within the AGB; j. using the distinction of the current eating pattern to modify the eating behavior of the patient.

22 Claims, 19 Drawing Sheets

(52) U.S. Cl.
CPC .......... *A61F 5/0053* (2013.01); *A61F 5/0056* (2013.01); *A61F 5/0059* (2013.01); *A61F 5/0063* (2013.01); *A61F 2005/002* (2013.01)

(56) References Cited

U.S. PATENT DOCUMENTS

| | | | |
|---|---|---|---|
| 2009/0192533 A1* | 7/2009 | Dlugos, Jr. | ............ A61B 5/037 606/157 |
| 2009/0222065 A1 | 9/2009 | Dlugos, Jr. et al. | |
| 2009/0306462 A1 | 12/2009 | Lechner | |
| 2010/0228080 A1 | 9/2010 | Tavori et al. | |
| 2011/0130625 A1 | 6/2011 | Lior et al. | |

OTHER PUBLICATIONS

International Preliminary Report on Patentability dated Dec. 17, 2013 for PCT/IL2012/000231.
Donald O. Castell MD, Andre Dubois MD Phd, Cynthia R. Davis BS, Carmel M. Cordova BS, and Douglas O. Norman BS; Computer-Aided Analysis of Human Esophageal Peristalsis; Digestive Diseases and Sciences; Jan. 1984; pp. 65-72; vol. 29; No. 1.
Andrew F. R. Dixon, John B. Dixon, and Paul E. O'Brien; Laparoscopic Adjustable Gastric Banding Induces Prolonged Satiety: A Randomized Blind Crossover Study; The Journal of Clinical Endocrinology & Metabolism; 2004; pp. 813-819; vol. 90; No. 2.
Wolfgang Lechner MD, Michael Gadenstatter MD MSC, Ruxandra Ciovica MD, Werner Kirchmayr MD, and Gerhard Schwab MD MBA; In Vivo Band Manometry: a New Access to Band Adjustment; Obesity Surgery; 2005; pp. 1432-1436; vol. 15.
Ass. Professor Martin Fried MD Phd, Wolfgang Lechner MD, and Karin Kormanova MD; Physical Principles of Available Adjustable Gastric Bands: How they Work; Obesity Surgery; 2004; pp. 1118-1122; vol. 14.
Martin Fried MD Phd; The current science of gastric banding: an overview of pressure-volume theory in band adjustments; Surgery for Obesity and Related Diseases; 2008; pp. S14-S21; vol. 4.
International Search Report (ISR) dated Dec. 20, 2012 for PCT/IL2012/000231 filed Jun. 13, 2012.
Written Opinion (WO) dated Dec. 20, 2012 for PCT/IL2012/000231 filed Jun. 13, 2012.
Martin Fried et al.; The Relationship Between Esophageal Peristalsis and In Vivo Intraband Pressure Measurements in Gastric Banding Patients; obes surg; 2010; pp. 1102-1109; vol. 20.

* cited by examiner

APPARATUS AND METHODS FOR CORRECTIVE GUIDANCE OF EATING BEHAVIOR

FIELD OF THE INVENTION

The present invention generally pertains to a system and method for corrective guidance of eating behavior.

BACKGROUND OF THE INVENTION

Morbid obesity is a chronic condition. Gastric limiting techniques (e.g. "adjustable gastric banding" or AGB) are employed by surgeons to treat morbidly obese people who cannot lose weight by traditional means. In AGB, a gastric "band" made of an elastomer is placed around the stomach near its upper end. This creates a small pouch with a narrow passage into the rest of the stomach ("stoma orifice"), thus limiting the amount of food intake ("eating") by creating a feeling of fullness or uneasiness and by usually extending the time frame required to empty the pouch into the rest of the stomach. To control the size of the stoma orifice, the gastric band can be pressurized or depressurized by a physician. As a non-limiting example, the pouch is usually of a size of 50 cc to 5 cc, preferably 20 cc to See, and more preferably of about 15 cc. The stoma size can be increased or decreased with a saline solution by using a needle and syringe to access a small access port placed under the skin. The stoma orifice is governed by the amount of stomach tissue inside the band at the banding site. A desired passage size is about 12 mm in internal diameter.

The aim of restricting passage of food and liquids is to force the patient to change his/her eating behavior and thereby to induce a significant amount of weight loss. Researchers have demonstrated that the initial weight loss results after AGB are less predictable then those after gastric bypass. Patients after surgery are advised to chew their food thoroughly, eat slowly, take small bites, avoid certain foods, etc. Often, a large number of these patients do not adopt the required behavior and instead, eat forcefully, vomit, and intermittently suffer stoma occlusion events. These may result eventually in such complications as pouch enlargement, band erosion, reflux, and esophageal enlargement. In some cases, additional surgical interventions may be required.

The observation of gastric band action and the adjusting of stoma orifice by inflation/deflation are facilitated by X-ray imaging. A physician or technician acts to adjust (increase or decrease) the volume of fluid in the band based on inputs from the X-ray imaging. The volume decrease is done by removing an amount of fluid from the band via the external access port and fill line. Alternatively, components for adjusting the size of the gastric band may be implanted within the patient and, when a physical parameter such as intra-band pressure related to the patient food passage is determined, an external control unit outside the patient's body may be operated to power the implanted components to adjust the size of the band.

Monitoring the activity of the pouch created between the lower esophagus sphincter and the gastric band may generate important information related to the eating behavior of patients. Physiological parameters obtained by such monitoring may be useful to help a patient control his/her obesity, manage his/her diabetes, and monitor his/her gastro-esophageal reflux disease and the like.

Adjustable gastric restriction devices with sensors and actuators which enable control of the stoma orifice are disclosed for example in US patent applications No. 20070156013 by Birk and 20060173238 by Starkebaum. Birk discloses a self-regulating gastric band with pressure data processing, relates to a band adjustment assembly which is provided for implanting with the gastric band that includes a sensor for sensing fluid pressure in the expandable portion. The band adjustment assembly further includes a pump assembly connected to the expandable portion and to a controller that can operate the pump assembly to adjust the volume of the fluid in the band based on the sensed fluid pressure. Starkebaum's invention relates to a dynamically controlled gastric occlusion device that monitors at least one physiological parameter that varies as a function of food intake and controls the degree of gastric constriction of an occluding device, such as a gastric band, based on the monitored physiological parameter. In an embodiment, the dynamically-controlled gastric occlusion device controls the degree of gastric constriction based on time. The occluding device is dynamically opened or closed to either permit or prevent the passage of food through the gastrointestinal (GI) tract.

A large number of studies have determined the following:
1) Pouch volume and stoma size are important determinants for the success of AGB.
2) Proper stoma adjustment can effect immediate and late results of the AGB and reduce complications such as Spherical Pouch Dilatation (SPD).
3) Fast eating or improper chewing of the food can lead to excessive pouch enlargement and impaired surgical results.
4) Adoption of favorable eating behavior is imperative for long term success of the AGB
5) Adoption of mal-eating behaviors can reduce the success rate of AGB.

Although gastric bands can limit food intake, it is worth recognizing that eating is a form of behavior that can be defined according to its structure (frequency duration and size of eating episodes). This pattern of behavior can be further analyzed at the level of a single meal, where the same structure (frequency duration and size of eating episodes—bites) rules and defines the meal size. In principle, this behavior operates through the skeletal musculature and is subject to conscious control. Therefore, people should be able to volitionally decide when and how to control their own eating. In practice, people find it extremely difficult to exert control and many obese people claim that their eating is out of (their) control.

AGB or other bariatric procedures such as: Gastric-By-Pass, Sleeve Gastrectomy, Vertical Banded Gastroplasty and Duodenal Switch, these procedures are not known to provide a patient with data or information regarding his/her eating behavior pattern, yet the patient is expected to adopt different eating behavior with respect to frequency, duration or size of bite or meal. The realization and visualization of eating behavior patterns is required to the patient in order to induce conscious and correct eating behavior modification. Therefore there is a need for a tool that will provide the AGB and other bariatric procedures obese patients a guided and controlled eating monitoring system and/or "pacer" that will enable them to learn and gain a new control over their eating behavior.

Out of the clinical literature from the last 15 years and over 500,000 patients with AGB it is clear that it is very difficult to obtain hard quantitative data on the true food intake behavior of AGB or other bariatric procedures obese patients. It is clear that in some AGB obese individuals, habitual food intake or its caloric value are greater than it is normally assumed to be and is often erratic and apparently unregulated. In order for health care givers to be able to advice and guide those patients to better regulate eating habits and behavior, there is clearly a need for a method and apparatus that will enable them to monitor and obtain objectively recorded eating behavior patterns. It would also be advantageous to have systems and methods to improve the action of AGB or other patients post bariatric procedures by automatically releasing excessive pressure buildups.

Fried, Surgery of Obesity and related diseases (2008 May-June) described the current science of gastric banding: "an overview of pressure-volume theory in band adjustments".

Fried et al in Obesity Surgery, 14, 2004 1121 measured intra band pressure on human subjects, using water as the swallowed medium, under fluoroscopy. In this study, the aim was to establish and compare stoma size and calibration with a low pressure-high, volume system, and a high pressure low volume system. The gastric space was towards the balloon of the band, which is responsible for stoma diameter maintenance. Pressure measurements were made in a patient with a low pressure-high volume band (SAGS), with baseline pressure of 40 mmHg There was an increase in pressure at the stoma region of up to 85 mmHg following a sip of water. A similar experiment is described by Fried et al in Obesity Surgery (2010 August) "The relationship between esophageal peristalsis and in vivo intraband pressure measurements in gastric banding patients".

Lechner at al describes in vivo band manometry as a new access to band adjustment focusing on optimal stoma size using a manometry, vs. volume calibration. (Obesity Surgery (2005 November-December).

Obrian et al in J Clin Endocrinol Metab, February 2005, 90(2):813-819, conducted measurements in human subjects for optimal band restriction. This study demonstrated that both fasting and postprandial feelings of satiety were significantly increased with optimal LAGB restriction compared with 2 days of reduced LAGB restriction. Importantly, these appetite changes were recorded within days in weight-stable individuals who had achieved significant weight loss, were the same weight at both tests, were blind to their band status, and after 14 h of fasting. Optimally restricted LAGB participants were also less hungry than BMI-matched controls. These findings strongly support the hypothesis that LAGB exerts an inhibitory effect on central appetite regulation, operating even during fasting.

Tavori. I, Fleicsher. L (WO/2009/050709) PCT/IL2008/001366 Apparatus and methods for corrective guidance of eating behavior after weight loss surgery is dealing with measuring influence of different food type on band pressure describe a device, system and method of providing corrective guidance to patients, post weight loss surgery using intraband pressure measurements.

However all of these depend on interpretation of the data by the clinician and therefore do not allow self-monitoring by the patient.

It is therefore a long felt need to provide a system and method of enabling the clinician and/or the patient to provide guidance to the patient on modifying eating habits.

SUMMARY OF THE INVENTION

It is an object of the present invention to disclose a system for guidance of eating behavior.

It is another object of the present invention to disclose a method for determining the consistency of food entering the stomach comprising steps of:

a. providing an adjustable gastric band (AGB);
b. providing a pressure sensor to measure pressure within said AGB;
c. providing a processing unit in communication with said pressure sensor, said processing unit containing instructions to collect at least one set of at least one pressure measurement and to analyze said at least one set of at least one pressure measurement;
d. providing a data base comprising data concerning pressure exerted within said AGB by a bolus of liquid food, a bolus of semiliquid food, and a bolus of solid food;
e. providing a means of recording said sets of at least one pressure measurements;
f. providing a means of recording the results of said analysis;
g. providing a means of communicating said results to at least one of a group consisting of a patient, a clinician, a doctor, a nurse, a dietician, and a researcher;
h. placing said AGB in position, said AGB at least partially surrounding a stoma orifice near the upper end of the stomach;
i. measuring said pressure within said AGB as said bolus of food passes through said stoma orifice;
j. analyzing said measured pressure; and
k. transmitting said results to at least one of a group consisting of a patient, a clinician, a doctor, a nurse, a dietician, and a researcher
thereby distinguishing between at least two of a group consisting of liquid food, semiliquid food, and solid food.

It is another object of the present invention to disclose a method for modifying the eating behavior of a patient equipped with a gastric restriction apparatus (GRA) comprising steps of:

a. providing an adjustable gastric band (AGB);
b. providing a pressure sensor to measure pressure within said AGB;
c. providing a processing unit in communication with said pressure sensor, said processing unit containing instructions to collect at least one set of at least one pressure measurement and to analyze said at least one set of at least one pressure measurement;
d. providing a data base comprising data concerning pressure exerted within said AGB by a bolus of liquid food, a bolus of semiliquid food, and a bolus of solid food;
e. providing a means of recording said sets of at least one pressure measurements;
f. providing a means of recording the results of said analysis;
g. providing a means of communicating said results to at least one of a group consisting of a patient, a clinician, a doctor, a nurse, a dietician, and a researcher;
h. placing said AGB in position, said AGB at least partially surrounding a stoma orifice near the upper end of the stomach;
i. measuring said pressure within said AGB as said bolus of food passes through said stoma orifice;
j. analyzing said measured pressure; and,
k. using said distinction of said current eating pattern to modify said eating behavior of said patient.

It is another object of the present invention to disclose the method for determining the consistency of food entering the stomach, additionally comprising a step of transmitting at least one of a group consisting of at least one of said least one set of at least one pressure measurement and said results to a location remote from said patient.

It is another object of the present invention to disclose the method for determining the consistency of food entering the stomach, additionally comprising a step of adapting the system alter itself in response to changes in at least one of a group consisting of food consistency, food granularity, bolus size, and duration of eating.

It is another object of the present invention to disclose the method for determining the consistency of food entering the stomach, additionally comprising a step of providing said bolus of liquid food comprising a standard formulation, said bolus of semiliquid food comprising of a standard formulation, and a bolus of solid food comprising a standard formulation.

It is another object of the present invention to disclose the method for determining the consistency of food entering the stomach, additionally comprising a step of providing a database of results of analyses of a plurality of sets of at least one pressure measurement of at least one bolus of liquid food, at least one bolus of semiliquid food, and at least one bolus of solid food.

It is another object of the present invention to disclose the method for determining the consistency of food entering the stomach, additionally comprising a step of making said distinction on the basis of a total factor, said total factor defined as Total factor $=g_1 \cdot F_{Peak} + g_2 \cdot F_{Area} + g_3 \cdot F_{Fade}$, said $g_i$ being weighting factors and said $F_i$ being local factors.

It is another object of the present invention to disclose the method for determining the consistency of food entering the stomach, additionally comprising a step of calculating said total factor a plurality of times, preferably three times, for each said bolus of food, once on the assumption that said food has the consistency of said liquid food, once on the assumption that said food has the consistency of said semiliquid food, and once on the assumption that said food has the consistency of said solid food.

It is another object of the present invention to disclose the method for determining the consistency of food entering the stomach, additionally comprising a step of limiting said weighting factors $g_i$ to be greater than or equal to zero and less than or equal to 1.

It is another object of the present invention to disclose the method for determining the consistency of food entering the stomach, additionally comprising a step of deriving said local factors $F_{Peak}$, $F_{Area}$ and $F_{Fade}$ from said at least one set of at least one pressure measurement.

It is another object of the present invention to disclose the method for determining the consistency of food entering the stomach, additionally comprising a step of limiting said local factors $F_{Peak}$, $F_{Area}$ and $F_{Fade}$ to be greater than or equal to zero and less than or equal to 1.

It is another object of the present invention to disclose the method for determining the consistency of food entering the stomach, additionally comprising a step of calculating said local factor $F_{Peak}$ from $$F_{Peak} = 1 - \frac{|Peak - \text{average Peak}|}{\frac{\sigma_{peak}}{2}},$$

Peak is the maximum pressure in one set of at least one pressure measurement, average Peak is the average maximum pressure of a plurality of sets of at least one pressure measurement, and $\sigma_{Peak}$ is the standard deviation of the average maximum pressure of a plurality of sets of at least one pressure measurement.

It is another object of the present invention to disclose the method for determining the consistency of food entering the stomach, additionally comprising a step of calculating said local factor $F_{Area}$ from $$F_{Area} = 1 - \frac{|Area - \text{average Area}|}{\frac{\sigma_{Area}}{2}},$$

Area is the area under the curve of pressure vs. time generated from the at least one set of at least one pressure measurement, average Area is the average area under the curve of pressure vs. time generated from a plurality of sets of at least one pressure measurement, and $\sigma_{Area}$ is the standard deviation of the average area under the curve of pressure vs. time generated from a plurality of sets of at least one pressure measurement.

It is another object of the present invention to disclose the method for determining the consistency of food entering the stomach, additionally comprising a step of calculating said local factor $F_{Fade}$ from $$F_{Fade} = 1 - \frac{1}{10} \frac{\sum_{j}^{i} [Pressure - \text{average Pressure}]}{j - i},$$

Pressure is pressure measurement at a time during the measurement of the at least one set of at least one pressure measurement, average Pressure is the average of pressure measurements at that time generated from a plurality of sets of at least one pressure measurement, j is the start time for the time period, and i is the end time for the time period.

It is another object of the present invention to disclose the method for determining the consistency of food entering the stomach, additionally comprising a step of selecting the start of said time period to be after the time at which the peak pressure occurs.

It is another object of the present invention to disclose the method for determining the consistency of food entering the stomach, additionally comprising a step of selecting the start of said time period to be after the time at which there is a minimum in the rate of change of pressure as a function of time.

It is another object of the present invention to disclose the method for determining the consistency of food entering the stomach, additionally comprising a step of selecting the start of said time period to be at a special point.

It is another object of the present invention to disclose the method for determining the consistency of food entering the stomach, additionally comprising a step of selecting said special point to be the intersection of the lines defining the slopes of two regions of approximately constant slope in the plot of rate of change of pressure as a function of time, said regions being after the minimum of the plot of rate of change of pressure as a function of time, said approximately constant slopes different from each other.

It is another object of the present invention to disclose the method for determining the consistency of food entering the stomach, additionally comprising a step of selecting the end of said time period to be the end of the set of at least one pressure measurement.

It is another object of the present invention to disclose the method for determining the consistency of food entering the stomach, additionally comprising a step of limiting said weighting factors $g_i$ to be greater than or equal to zero and are less than or equal to one.

It is another object of the present invention to disclose the method for determining the consistency of food entering the stomach, additionally comprising a step of setting the sum of said weighting factors $g_i$ to one, $g1+g2+g3=1$.

It is another object of the present invention to disclose the method for determining the consistency of food entering the stomach, additionally comprising a step of setting said weighting factors $g_i$ to be equal, $g1=g2=g3=\frac{1}{3}$.

It is another object of the present invention to disclose the method for determining the consistency of food entering the stomach, additionally comprising a step of conditioning said pressure measurement data with a Butterworth low pass filter.

It is another object of the present invention to disclose the method for determining the consistency of food entering the stomach, additionally comprising a step of conditioning said pressure measurement data with a gain factor G, $$G = \frac{1}{\sqrt{1+(2f)^4}},$$

$f=\frac{1}{2}$.

It is another object of the present invention to disclose the method for determining the consistency of food entering the stomach, additionally comprising a step of selecting a criterion value to carry out said distinguishing.

It is another object of the present invention to disclose the method for determining the consistency of food entering the stomach, additionally comprising a step of setting said criterion to a value greater than approximately 0.2 and less than approximately 0.4.

It is another object of the present invention to disclose the method for determining the consistency of food entering the stomach, additionally comprising a step of setting said criterion value to a value approximately 0.246.

It is another object of the present invention to disclose the method for determining the consistency of food entering the stomach, additionally comprising a step of determining said consistency of said bolus of food, wherein said bolus of food has consistency approximately the same as said bolus of said standard food if said total factor calculated assuming said food has the consistency of said standard food is greater than said criterion value.

It is another object of the present invention to disclose the method for determining the consistency of food entering the stomach, additionally comprising a step of providing an eating behavior pattern descriptive report based on the analysis of at least one eating parameter selected from a group consisting of constant speed eater, fast or accelerated speed eater, night eater, binge eater, total size of meal, average volume of meal, and average time of meal, volumetric consumption by time, shifting to liquid food consumption, vomiting events, type of food consumed, meal times during the day and duration, new adjustment validation data and short/long term change of pressure events as a result of new adjustment or any combination thereof.

It is another object of the present invention to disclose the method for determining the consistency of food entering the stomach, additionally comprising a step of providing means adapted to indicate said current eating behavior through a display to the patient.

It is another object of the present invention to disclose the method for determining the consistency of food entering the stomach, additionally comprising a step of monitoring at least one current eating behavior parameter.

It is another object of the present invention to disclose the method for determining the consistency of food entering the stomach, additionally comprising a step of calibrating said GRA to a desired restriction based on said monitored parameter.

It is another object of the present invention to disclose the method for determining the consistency of food entering the stomach, additionally comprising a step of indicating said eating behavior pattern to at least one selected from a group consisting of (a) said patient; (b) a predetermined clinician; or any combination thereof.

It is another object of the present invention to disclose the method for determining the consistency of food entering the stomach, additionally comprising a step of performing said indication by at least one selected from a group consisting of (a) said patient; (b) a predetermined clinician through appropriate instructions to said patient.

It is another object of the present invention to disclose the method for determining the consistency of food entering the stomach, additionally comprising a step of adapting said system to identify at least one of a group consisting of: what type of food is the patient consuming; how many meals does the patient have per day; is the patient chewing the food sufficiently; were there vomiting events following the calibration; after recalibrating, is the current stoma adjusted to the patient's need; what are meal durations; what are the intervals between each bite and do they correspond with the pouch emptying time; is the patient a fast eater; is the patient a night eater; what kind of food is eaten at night; does the patient drink during the meal; is there a change in the patient's pressure regime since the last calibration.

It is another object of the present invention to disclose the method for determining the consistency of food entering the stomach, additionally comprising a step of adapting said system to identify variability in said patient's eating habits.

It is another object of the present invention to disclose the method for determining the consistency of food entering the stomach, additionally comprising a step of adapting said system to warn to said patient if proper eating protocols are not being followed.

It is another object of the present invention to disclose a system for determining the consistency of food comprising:
  a. An adjustable gastric band (AGB);
  b. A pressure sensor to measure pressure within said AGB;
  c. a processing unit in communication with said pressure sensor, said processing unit containing instructions to collect at least one set of at least one pressure measurement and to analyze said at least one set of at least one pressure measurement;
  d. a data base comprising data concerning pressure exerted within said AGB by a bolus of liquid food, a bolus of semiliquid food, and a bolus of solid food;
  e. a means of recording said pressure measurements;
  f. a means of recording the results of said analysis; and
  g. a means of communicating said results to at least one of a group consisting of a patient, a clinician, a doctor, a nurse, a dietician, and a researcher whereby said processing unit is adapted to provide output data distinguishing between at least two of a group consisting of liquid food, semiliquid food, and solid food.

It is another object of the present invention to disclose a system for modifying the eating behavior of a patient equipped with a gastric restriction apparatus comprising:
a. at least one adjustable gastric band (AGB);
b. at least one pressure sensor to measure pressure within said AGB;
c. at least one processing unit in communication with said pressure sensor, said processing unit containing instructions to collect at least one set of at least one pressure measurement and to analyze said at least one set of at least one pressure measurement;
d. at least one data base comprising data concerning pressure exerted within said AGB by a bolus of liquid food, a bolus of semiliquid food, and a bolus of solid food;
e. at least one means of recording said pressure measurements;
f. at least one means of recording the results of said analysis; and
g. at least one means of using said distinction of said current eating pattern to modify said eating behavior of said patient.

It is another object of the present invention to disclose the system for determining the consistency of food, wherein at least one of said at least one of a group consisting of at least one of said least one set of at least one pressure measurement and said results are transmitted to a location remote from said patient.

It is another object of the present invention to disclose the system for determining the consistency of food, wherein the system can alter itself in response to changes in at least one of a group consisting of food consistency, food granularity, bolus size, and duration of eating.

It is another object of the present invention to disclose the system for determining the consistency of food, wherein said bolus of liquid food comprises a standard formulation, said bolus of semiliquid food comprises a standard formulation, and a bolus of solid food comprises a standard formulation.

It is another object of the present invention to disclose the system for determining the consistency of food, additionally comprising a database of results of analyses of a plurality of sets of at least one pressure measurement of at least one bolus of liquid food, at least one bolus of semiliquid food, and at least one bolus of solid food.

It is another object of the present invention to disclose the system for determining the consistency of food, wherein said distinction is made on the basis of a total factor, said total factor defined as Total factor $=g_1 \cdot F_{Peak} + g_2 \cdot F_{Area} + g_3 \cdot F_{Fade}$, said $g_i$ being weighting factors and said $F_i$ being local factors.

It is another object of the present invention to disclose the system for determining the consistency of food, wherein said total factor is calculated a plurality of times, preferably three times, for each said bolus of food, once on the assumption that said food has the consistency of said liquid food, once on the assumption that said food has the consistency of said semiliquid food, and once on the assumption that said food has the consistency of said solid food.

It is another object of the present invention to disclose the system for determining the consistency of food, wherein said weighting factors $g_i$ are greater than or equal to zero and less than or equal to 1.

It is another object of the present invention to disclose the system for determining the consistency of food, wherein said local factors $F_{Peak}$, $F_{Area}$ and $F_{Fade}$ are derived from said at least one set of at least one pressure measurement.

It is another object of the present invention to disclose the system for determining the consistency of food, wherein said local factors $F_{Peak}$, $F_{Area}$ and $F_{Ride}$ are greater than or equal to zero and less than or equal to 1.

It is another object of the present invention to disclose the system for determining the consistency of food, wherein said local factor $F_{Peak}$ is calculated from $$F_{Peak} = 1 - \frac{|Peak - \text{average Peak}|}{\frac{\sigma_{peak}}{2}},$$

Peak is the maximum pressure in one set of at least one pressure measurement, average Peak is the average maximum pressure of a plurality of sets of at least one pressure measurement, and $\sigma_{Peak}$ is the standard deviation of the average maximum pressure of a plurality of sets of at least one pressure measurement.

It is another object of the present invention to disclose the system for determining the consistency of food, wherein said local factor $F_{Area}$ is calculated from $$F_{Area} = 1 - \frac{|Area - \text{average Area}|}{\frac{\sigma_{Area}}{2}},$$

Area is the area under the curve of pressure vs. time generated from the at least one set of at least one pressure measurement, average Area is the average area under the curve of pressure vs. time generated from a plurality of sets of at least one pressure measurement, and $\sigma_{Area}$ is the standard deviation of the average area under the curve of pressure vs. time generated from a plurality of sets of at least one pressure measurement.

It is another object of the present invention to disclose the system for determining the consistency of food, wherein said local factor $F_{Fade}$ is calculated from $$F_{Fade} = 1 - \frac{1}{10} \frac{\sum_{j}^{i} [\text{Pressure} - \text{average Pressure}]}{j - i},$$

Pressure is pressure measurement at a time during the measurement of the at least one set of at least one pressure measurement, average Pressure is the average of pressure measurements at that time generated from a plurality of sets of at least one pressure measurement, j is the start time for the time period, and i is the end time for the time period It is another object of the present invention to disclose the system for determining the consistency of food, wherein the start of said time period occurs after the time at which the peak pressure occurs.

It is another object of the present invention to disclose the system for determining the consistency of food, wherein the start of said time period occurs after the time at which there is a minimum in the rate of change of pressure as a function of time.

It is another object of the present invention to disclose the system for determining the consistency of food, wherein the start of said time period occurs at a special point.

It is another object of the present invention to disclose the system for determining the consistency of food, wherein said special point is the intersection of the lines defining the slopes of two regions of approximately constant slope in the plot of rate of change of pressure as a function of time, said regions being after the minimum of the plot of rate of change of pressure as a function of time, said approximately constant slopes different from each other.

It is another object of the present invention to disclose the system for determining the consistency of food, wherein the end of said time period is the end of the set of at least one pressure measurement.

It is another object of the present invention to disclose the system for determining the consistency of food, wherein said weighting factors gi are greater than or equal to zero and are less than or equal to one.

It is another object of the present invention to disclose the system for determining the consistency of food, wherein the sum of said weighting factors $g_i$ is one, $g_1+g_2+g_3=1$.

It is another object of the present invention to disclose the system for determining the consistency of food, wherein said weighting factors $g_i$ are all equal, $g_1=g_2=g_3=\frac{1}{3}$.

It is another object of the present invention to disclose the system for determining the consistency of food, wherein said pressure measurement data are conditioned with a Butterworth low pass filter.

It is another object of the present invention to disclose the system for determining the consistency of food, wherein said pressure measurement data are conditioned with a gain factor G, $$G = \frac{1}{\sqrt{1+(2f)^4}},$$

$f=\frac{1}{2}$.

It is another object of the present invention to disclose the system for determining the consistency of food, wherein said distinguishing is carried out by means of a criterion value.

It is another object of the present invention to disclose the system for determining the consistency of food, wherein said criterion value is greater than approximately 0.2 and less than approximately 0.4.

It is another object of the present invention to disclose the system for determining the consistency of food, wherein said criterion value is approximately 0.246.

It is another object of the present invention to disclose the system for determining the consistency of food, wherein said bolus of food has consistency approximately the same as said bolus of said standard food if the total factor calculated assuming said food has the consistency of said standard food is greater than said criterion value.

It is another object of the present invention to disclose the system for determining the consistency of food, wherein an eating behavior pattern descriptive report is provided based on the analysis of at least one current eating behavior parameter selected from a group consisting of constant speed eater, fast or accelerated speed eater, night eater, binge eater, total size of meal, average volume of meal, and average time of meal, volumetric consumption by time, shifting to liquid food consumption, vomiting events, type of food consumed, meal times during the day and duration, new adjustment validation data and short/long term change of pressure events as a result of new adjustment or any combination thereof.

It is another object of the present invention to disclose the system for determining the consistency of food, additionally comprising means to indicate said current eating behavior through a display to the patient.

It is another object of the present invention to disclose the system for determining the consistency of food, additionally comprising means to monitor at least one current eating behavior parameter.

It is another object of the present invention to disclose the system for determining the consistency of food, wherein said GRA is calibrated to a desired restriction based on said monitored parameter.

It is another object of the present invention to disclose the system for determining the consistency of food, additionally comprising means adapted to indicate said eating behavior pattern to at least one selected from a group consisting of (a) said patient; (b) a predetermined physician; or any combination thereof.

It is another object of the present invention to disclose the system for determining the consistency of food, wherein said indication is performed by at least one selected from a group consisting of (a) the patient; (b) said physician through appropriate instructions to said patient.

It is another object of the present invention to disclose the system for determining the consistency of food, wherein said system can identify at least one of a group consisting of: what type of food is the patient consuming; how many meals does the patient have per day; is the patient chewing the food sufficiently; were there vomiting events following the calibration; after recalibrating, is the current stoma adjusted to the patients need; what are meal durations; what are the intervals between each bite and do they correspond with the pouch emptying time; is the patient a fast eater; is the patient a night eater; what kind of food is eaten at night; does the patient drink during the meal; is there a change in the patients pressure regime since the last calibration.

It is another object of the present invention to disclose the system for determining the consistency of food, wherein said system can identify variability in the patient's eating habits.

It is another object of the present invention to disclose the system for determining the consistency of food, wherein the system comprises a warning to the patient if proper eating protocols are not being followed.

BRIEF DESCRIPTION OF THE FIGURES

In order to better understand the invention and its implementation in practice, a plurality of embodiments will now be described, by way of non-limiting example only, with reference to the accompanying drawings, wherein FIG. 1 schematically illustrates an embodiment of the system of the present invention.

DETAILED DESCRIPTION OF THE PREFERRED EMBODIMENTS

Figure 1:
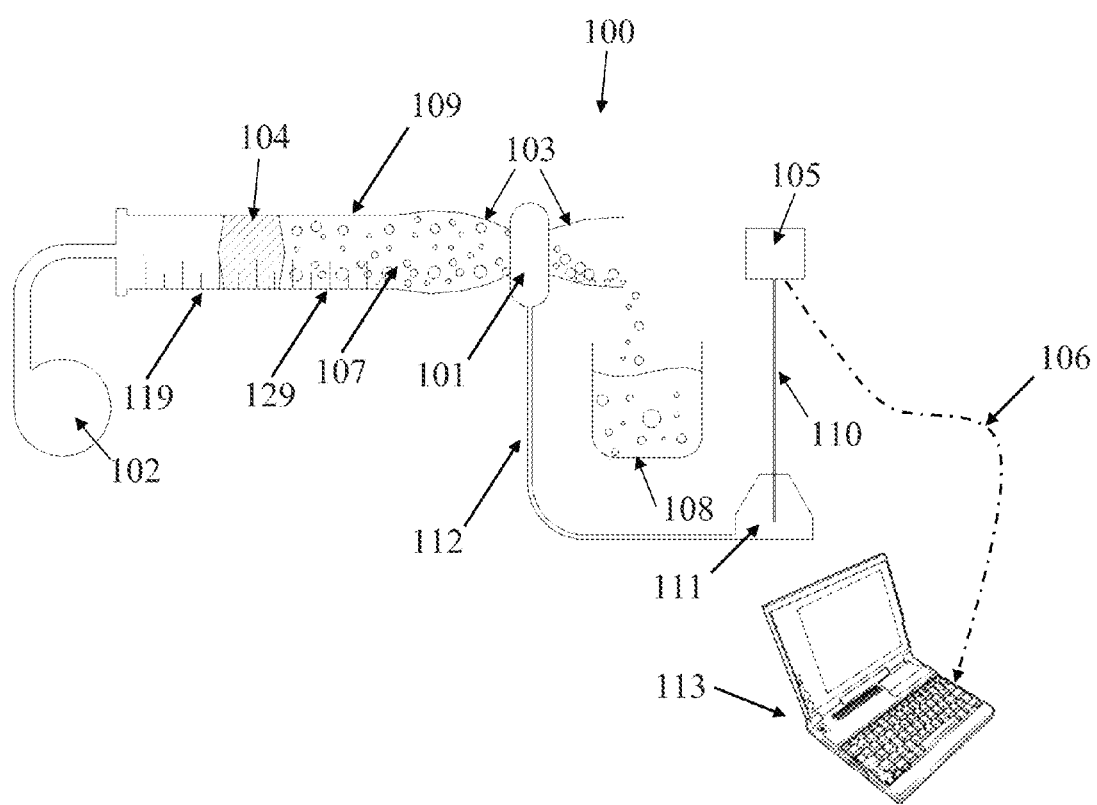

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for corrective guidance of eating behavior.

The present invention provides a system for modifying the eating behavior of a patient equipped with a gastric restriction apparatus comprising:
 a. at least one adjustable gastric band (AGB);
 b. at least one pressure sensor to measure pressure within said AGB;
 c. at least one processing unit in communication with said pressure sensor, said processing unit containing instructions to collect at least one set of at least one pressure measurement and to analyze said at least one set of at least one pressure measurement;
 d. at least one data base comprising data concerning pressure exerted within said AGB by a bolus of liquid food, a bolus of semiliquid food, and a bolus of solid food;
 e. at least one means of recording said pressure measurements;
 f. at least one means of recording the results of said analysis; and
 g. at least one means of using said distinction of said current eating pattern to modify said eating behavior of said patient.

The present invention further provides a method for modifying the eating behavior of a patient equipped with a gastric restriction apparatus (GRA) comprising steps of:
 a. providing an adjustable gastric band (AGB);
 b. providing a pressure sensor to measure pressure within said AGB;
 c. providing a processing unit in communication with said pressure sensor, said processing unit containing instructions to collect at least one set of at least one pressure measurement and to analyze said at least one set of at least one pressure measurement;
 d. providing a data base comprising data concerning pressure exerted within said AGB by a bolus of liquid food, a bolus of semiliquid food, and a bolus of solid food;
 e. providing a means of recording said sets of at least one pressure measurements;
 f. providing a means of recording the results of said analysis;
 g. providing a means of communicating said results to at least one of a group consisting of a patient, a clinician, a doctor, a nurse, a dietician, and a researcher;
 h. placing said AGB in position, said AGB at least partially surrounding a stoma orifice near the upper end of the stomach;
 i. measuring said pressure within said AGB as said bolus of food passes through said stoma orifice;
 j. analyzing said measured pressure; and,
 k. using said distinction of said current eating pattern to modify said eating behavior of said patient.

The term 'adjustable gastric band' (AGB) hereinafter refers to a medical device designed to be placed around the stomach via surgery, in order to treat obesity. May also be referred as "band", "Intraband" or "Lap band".

The term 'bolus' hereinafter refers to a mass of chewed food traveling from the mouth to the stomach, or an artificial imitation thereof.

The term 'Stoma orifice' hereinafter refers to the aperture created by the AGB in the stomach entrance. May also be called "Stoma".

The term 'body mass index' (BMI) hereinafter refers to a measure of obesity, defined as $$\text{Body Mass Index} = \frac{\text{weight[kg]}}{(\text{Height[m]})^2}.$$

The term 'Saline' hereinafter refers to an isotonic water based solution containing sodium chloride (NaCl).

The term 'Obesity' hereinafter refers to a medical condition in which excess fat is present, clinically defined as a $$BMI \geq 30 \frac{\text{kg}}{\text{m}^2}.$$

The term 'in vitro' hereinafter refers to in the lab.

The term 'in vivo' hereinafter refers to in a living patient.

The term 'Rheology' hereinafter refers to the study of the flow of matter, primarily flow of non Newtonian fluids.

The term 'Lower Esophageal Sphincter' (LES) hereinafter refers to part of the stomach attached to the esophagus.

The term 'fading rate' hereinafter refers to the rate at which the pressure decreases as a function of time during and after passage of a bolus of food.

The term 'signal' hereinafter refers to the pressure vs. time data for passage of a single bolus of food through an AGB.

The term 'plurality' hereinafter refers to any integer greater than 1.

The subscript '$_i$' hereinafter refers to any one of a plurality of terms. For example, $g_i$ refers to any of $g_1$, $g_2$ or $g_3$ and $F_t$ refers to any of $F_{Peak}$, $F_{Area}$ and $F_{Fade}$.

The term 'approximately' hereinafter refers to a difference of about 25%.

The term 'GUI' hereinafter refers to a graphical user interface.

The term 'A to D' hereinafter refers to the Analog to Digital signal processing method whereby analog signals are converted to digital signals.

This system provides a fundamental tool for assessment of consumed food, by making pressure measurements related to the pressure inside the band while "swallowing" and finding the characteristic nature of pressure as a function of the "swallowed" substance, and thereby to distinguish between different consistencies and granularities of food passing through a small pouch and a stoma simulator.

The embodiment described herein simulates the body environment, including esophageal peristaltic waves at the lower end of the esophagus, the small pouch above the stoma formed by the adjustable gastric band (AGB), the chewed substance that travels from the mouth through the esophagus to the stomach and the Lower Esophageal Sphincter (LES). The importance of intra band measurements to indicate no LES peristaltic motion may indicate also complications such as band slippage, band erosion etc.

The experiments conducted hereinbelow in the examples described hereinbelow used the following imitation food compounds: a liquid composition, a semiliquid composition and a solid composition. Bolus sizes were in the range 5 ml or 10 ml. The experimental requirements used are given in Table 1.

TABLE 1

Experimental requirements

| Food imitation consistency | Food characteristics 5 [ml] or 10[ml] | Number of experiments | Number of peristaltic pulse repetitions |
|---|---|---|---|
| Liquid | 5 | 30 | Up to 8 |
| Semi-liquid | 5 | 30 | Up to 8 |
| Solid | 5 | 30 | Up to 8 |

The experiments in the examples disclosed hereinbelow were conducted at a temperature of 37° C., and the temperature was checked regularly and corrected if necessary. Pressures were kept in the range 0-120 mmHg.

The system in the examples disclosed hereinbelow is capable of operating in combined temperature and humidity conditions of 20-40 deg C. at 10%-90% RH.

The system in the examples disclosed hereinbelow is equipped to present results, communicate the results and generate reports to the clinician: on an LCD, on the clinician's office equipment, on a PC, on a Printer, etc. It is also capable of detecting and presenting to the clinician operational faults such as:

Band pressure is above 180[mmHg], Band pressure and time curve is above 180 mmHg, and 180 seconds. The threshold is user programmable. In preferred embodiments, the user is limited to a clinician, e.g., a doctor, nurse, researcher or other authorized person.

If communication fails, data will be stored in machine's memory at least until communication returns The software will announce operational stage and operation time on machine's LCD or clinician's PC (Optional).

The software will be able to combine patient data into final results, received either via a GUI from physician's PC, or the machine onboard keyboard. This information includes time, date, patient personal information such as name and identity number.

In another embodiment, the system in the examples disclosed hereinbelow is equipped to present results, and generate reports to the clinician: on an LCD, on the clinician's office equipment, on a PC, on a Printer, etc. It is also capable of detecting and presenting to the clinician operational faults such as:

Band pressure is above 180[mmHg], Band pressure and time curve is above 180 mmHg, and 180 seconds. The threshold is user programmable. In preferred embodiments, the user is limited to a clinician, e.g., a doctor, nurse, researcher or other authorized person.

The software will announce operational stage and operation time on machine's LCD or clinician's PC (Optional).

The software will be able to combine patient data into final results, received either via a GUI from physician's PC, or the machine onboard keyboard. This information includes time, date, patient personal information such as name and identity number.

In all of the Figures, identical numbers refer to similar functions.

In reference to FIG. 1, a schematic diagram of one embodiment of a variant of the system (100), for in vitro testing, is shown. The system comprises a rigid, impermeable tube (109) fluidly connected to a flexible, impermeable tube (103) which simulates the body tissue of the small pouch in the stomach (203) above the AGB (101) and a portion of the stomach (203) below the AGB, and a pressure source (102). For non-limiting example, the flexible, impermeable tube is a Penrose drain which has good dimensional stability and high mechanical flexibility. A movable plunger (104) divides the rigid tube (109), which functions as a separation chamber, into two segments, an upstream segment (119) fluidly connected to the pressure source (102) and a downstream segment (129) fluidly connected to the flexible, impermeable tube (103). In this embodiment, the pressure source is a cardiovascular pump, for non-limiting example a cardiovascular pump made by Hemodynamic Israel. However any pulsatile power source such as, for non-limiting example, a peristaltic pump, capable of generating the required imitation of food passage via the stoma produced by an occluding device such as an AGB can be used. The upstream segment (119) contains the working fluid for the cardiovascular pump, in this embodiment, water. The downstream segment (129) and the flexible tube (103) contain the experimental medium (107). Surrounding a portion of the flexible tube (103) is an adjustable gastric band (101) (AGB). Downstream of the AGB is an outlet container (108) to contain used experimental medium (107). In this embodiment, the pressure measurement system comprises an access port (111), a Huber needle (110) and a pressure gauge (105). The access port (111) is fluidly connected to the AGB (101) via connection tube (112), and allows access by the Huber needle (110) to the interior of the AGB (101) so that the pressure inside the AGB (101) can be measured. The Huber needle transmits the pressure to the pressure gauge (105). The pressure gauge (105) is connected via a USB cable (106) or other suitable connector to a data processor (113), preferably a PC.

In some embodiments, the AGB is a standard off the shelf band, of a model commonly used in actual adjustable gastric banding weight loss surgeries. The band itself, the tube and the access port contains water while the pressure is measured through a needle inserted through the access port.

Figure 2:
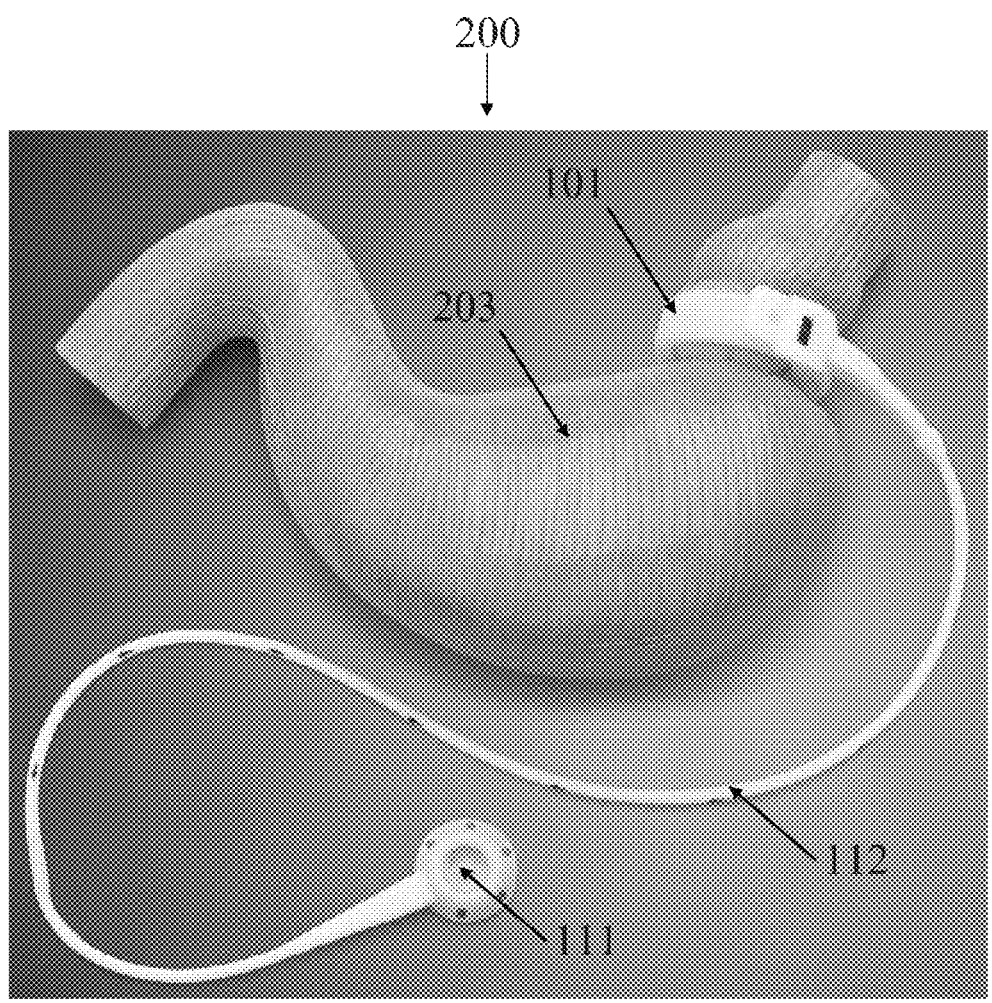
FIG. 2 depicts an adjustable gastric band in position around a model of the stomach.

In reference to FIG. 2, part of the system (200) is shown. In FIG. 2, an AGB (101) typical of those commonly used for bariatric surgery is depicted in a position typical of that in which it would be placed in a living patient, shown around a model of the stomach (203). In FIG. 2, the access port (111) is shown, connected to the AGB (101) via connection tube 112. When the AGB is used on living patients, the access port will be just inside or just outside the skin of the patient, allowing fluid to be added to or removed from the AGB (101) and allowing the pressure inside the AGB (101) to be measured without harming the patient.

In preferred embodiments, the fluid pressurizing the AGB (101) is saline. In preferred embodiments, a pressure gauge is selected which allows measurement of pressure of a liquid medium, for non-limiting example, the General-Electric NPC-100 series disposable blood pressure gauge with a measurement error of ±1%. In many embodiments, the signal from the pressure gauge requires amplification, as is the case for the exemplary gauge described hereinabove. A non-limiting example of a signal amplifier is the BURR-BROWN INA 122 amplifier commonly used in ECG (Electrocardiogram) machines for signal amplification. Data acquisition software is also required. For non-limiting example, data can be acquired via a standard National Instruments Data Acquisition (NI-DAQ) analog to digital (A to D) converter with a sampling frequency of 1 kHz and range of [+/−10v] and digitized data transmitted to a PC running the National Instruments GUI via a USB cable linked to the A to D converter. The USB cable is exemplary. Any suitable communication system may be used, for example, wired, audio, optical or wireless, using any communication protocol such as RS-232, RS 422, IP, HTML, XML and the like. The communication may be one way, or it may be two way, allowing both data upload and download.

Uploading is calibrating the device or system to a patient, including average bolus size, pressure behavior for a standard meal, personal information, and the like, where downloading is retrieving data from the system.

The output of the A to D converter is a voltage; calibration was performed to convert the calibration into pressure.

Figure 3:
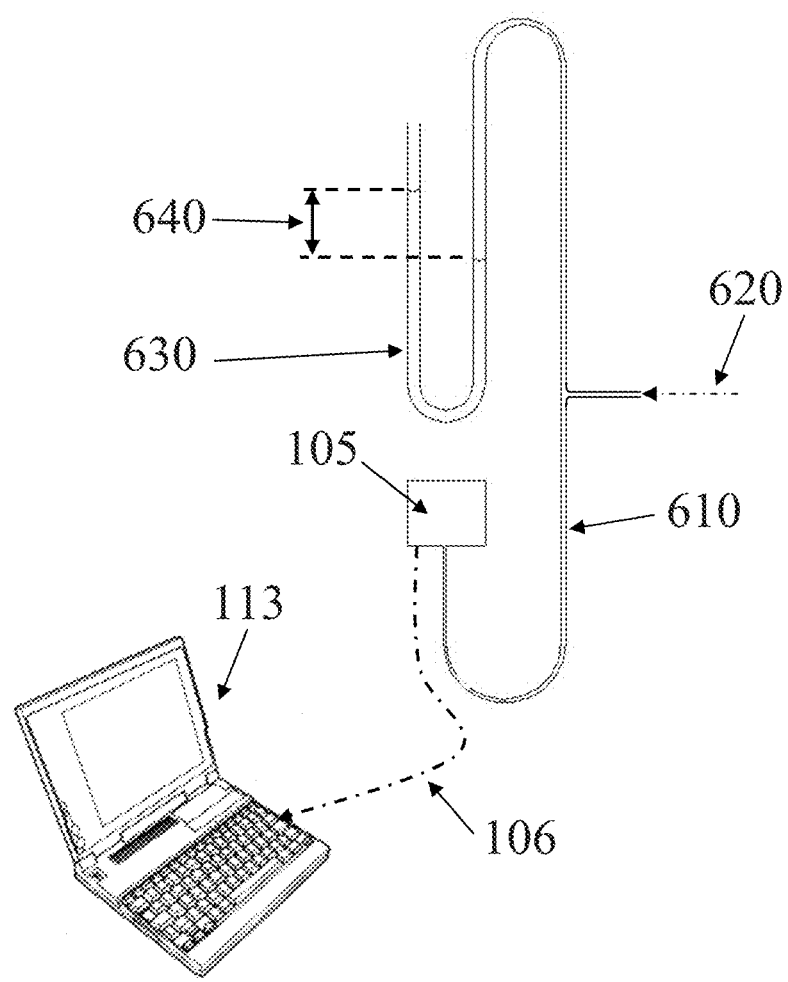
FIG. 3 schematically illustrates a method of calibrating the pressure sensor in the present invention.

In reference to FIG. 3, a standard Mercury U-tube manometer (630) can be used as a reference standard. The pressure gauge (105) was fluidly connected to an airline (610) and to the manometer (630). Air (620) was used to pressurize the system. The output of the pressure gauge (105) was transmitted to the PC 113 via the USB line (106). The pressure was read in mm Hg (640) from the manometer (630).

Figure 4:
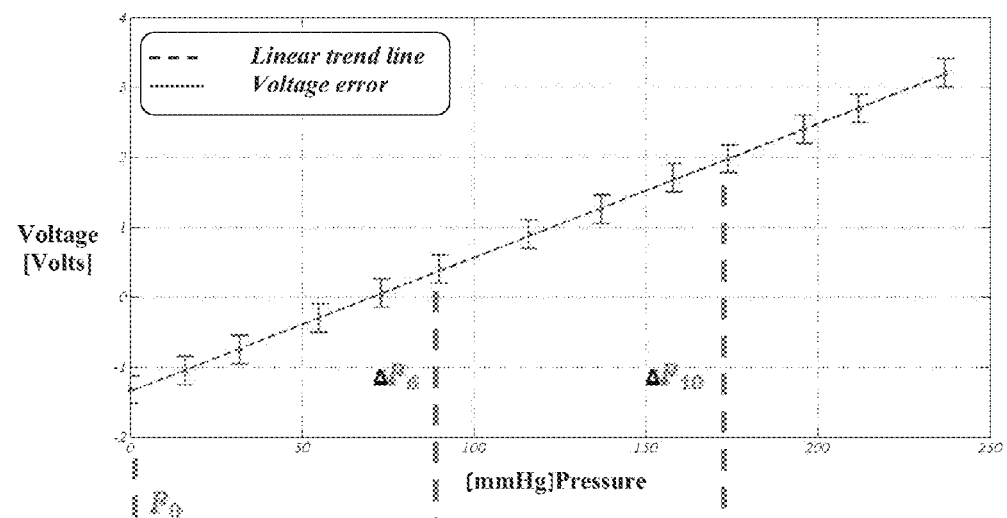
FIG. 4 schematically illustrates part of a method of calibrating the pressure sensor in the present invention.
Figure 4:
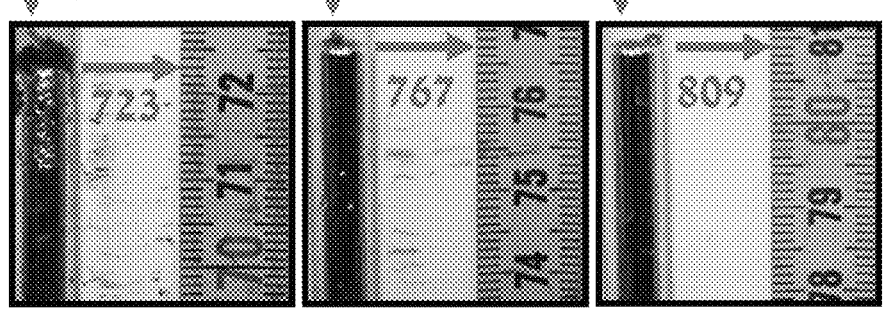

In reference to FIG. 4, FIG. 4A depicts the calibration curve, while FIGS. 4B-4D depict photographs of the manometer readings for selected pressures. In FIG. 4A, the horizontal error bars are not shown. At ±1 mm Hg, they would be barely visible. The horizontal scale in FIG. 4A shows the pressure relative to the base pressure $P_0$ (the gauge pressure), while the manometer readings in FIGS. 4B-4D show the absolute pressure. Two examples of the calculation of the relative pressure are:

$$\Delta P_6 = 2(P_6 - P_0) = 2(767 - 723) = 88 \pm 1 \text{ [mmHg]}$$

$$\Delta P_{10} = 2(P_{10} - P_0) = 2(609 - 723) = 172 \pm 1 \text{ [mmHg]}$$

$$\Delta P_{10\ 12} = (P_{10} - P_0) = 2(809 - 723) = 172 \pm 1 \text{ [mmHg]}$$

The factor of two occurs because the manometer is set up to read the height of one column above its base value; the total height difference is twice that, as the second column will be the same amount below the base value.

There are 13 measurements in total. The linear trend line is generated to fit the 13 measurements using a least squares method, giving a linear trend line equation of:

$$V = (0.01913)P - 1.3438, \quad (1)$$

where V is the Voltage[Volts] and P is the Pressure in [mmHg].

Figure 5:
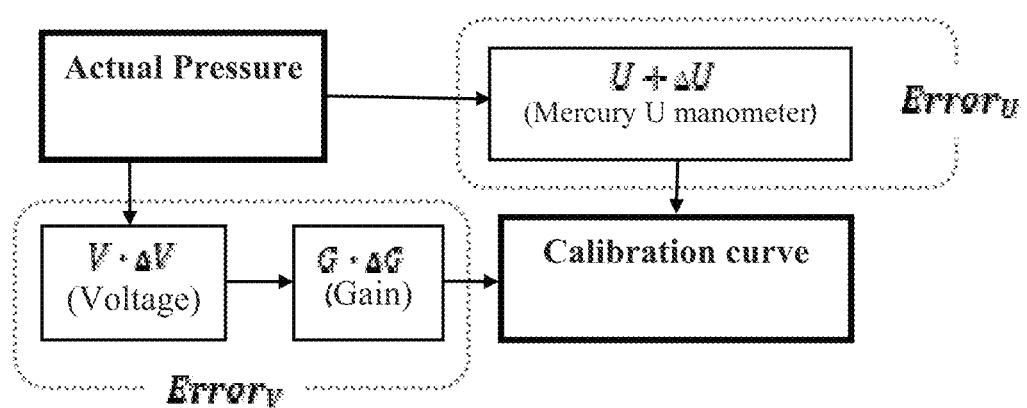
FIG. 5 schematically illustrates a flow chart of a method of accounting for measurement errors in the pressure calibration.

In reference to FIG. 5, a flow diagram of the error calculation is shown. The actual pressure generates a reading on the manometer, which has an error $\Delta U$. It also generates a reading on the pressure gauge, which has an error in the voltage $\Delta V$ and an error in the gain $\Delta G$. These errors must be combined to find the error in the calibration curve. The maximum error in the calibration curve is then calculated as follows:

Pressure gauge error: $\Delta V = 1\%$

Amplifier error: $\Delta G = 0.3\%$

Mercury manometer error: $\Delta U = \pm 1$ [mmHg]

Error function: $f_{(V \cdot G)} = V \cdot G$

Gain: $G = 20$ $$Error_V = \pm \sqrt{\left(\frac{\partial f}{\partial V} \Delta V\right)^2 + \left(\frac{\partial f}{\partial G} \Delta G\right)^2} \quad (2)$$

$$= \pm \sqrt{(G \cdot \Delta V)^2 + (V \cdot \Delta G)^2},$$

As an example, for point number 6:

$$V_6 = 0.4 \text{[Volts]}$$

$$Error_{V_6} = \pm \sqrt{(G \cdot \Delta V)^2 + (V \cdot \Delta G)^2}$$

$$= \pm \sqrt{(20 \cdot 0.01)^2 + (0.4 \cdot 0.003)^2}$$

$$Error_{V_6} = \pm 0.2$$

$$Error_{V_6} = \pm 0.2$$

EXAMPLE 1

The objective of the example is to simulate the passage of bolus of food through the AGB and to record the pressure during the passage for later analysis. The experimental media used are 3 different types of standardized food, each type having different liquid percentages and different properties of granularity. They will be called A, B and C.

$$A \rightarrow \frac{1}{10} \frac{\text{Granulate}}{\text{liquid}};$$

$$B \rightarrow \frac{1}{5} \frac{\text{Granulate}}{\text{liquid}};$$

$$C \rightarrow \frac{1}{15} \frac{\text{Granulate}}{\text{liquid}}$$

Figure 6:
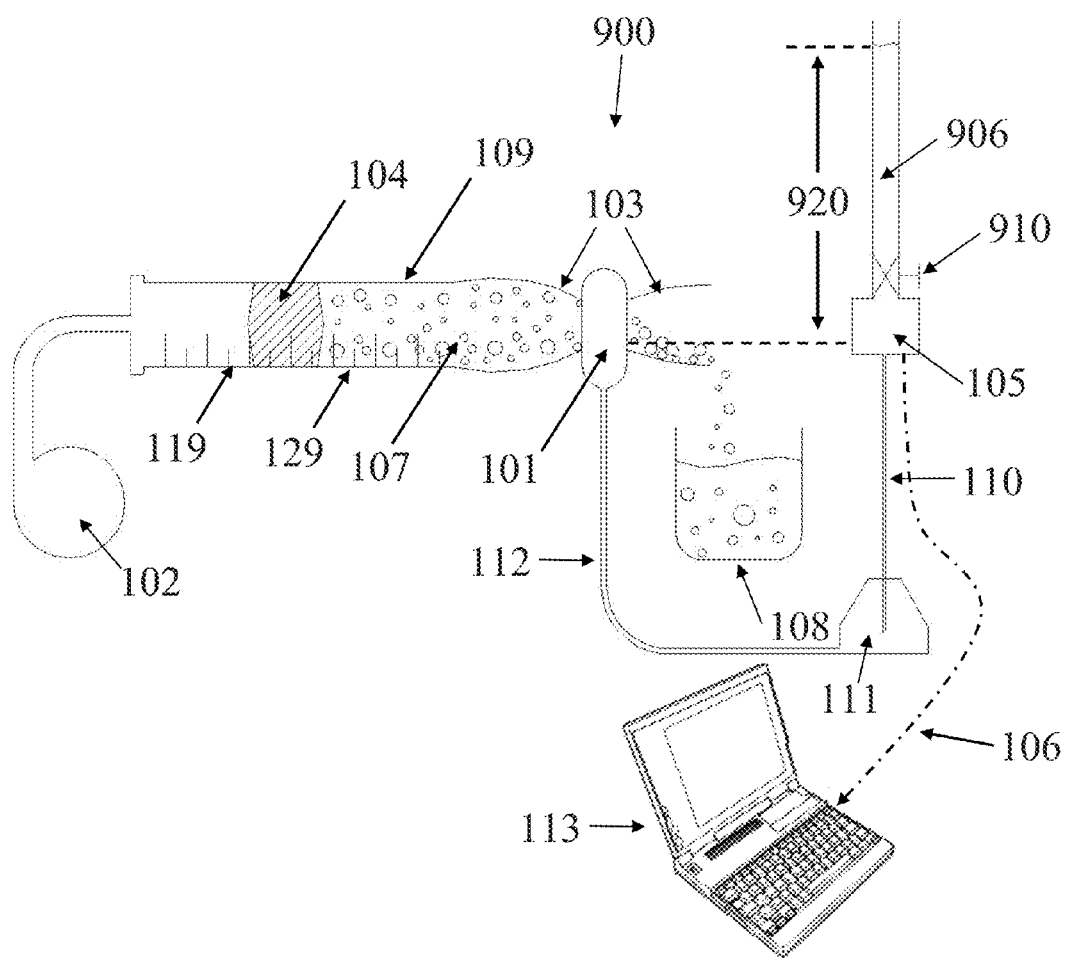
FIG. 6 schematically illustrates an embodiment of the system of the present invention.

In reference to FIG. 6, a schematic of another embodiment (900) of the system is shown, the embodiment used in Example 1. The system comprises a rigid, impermeable tube (109)), which functions as a separation chamber, fluidly connected to a flexible, impermeable tube (103) and a pressure source (102). A movable plunger (104) divides the rigid tube (109) into two segments, an upstream segment (119) fluidly connected to the pressure source (102) and a downstream segment (129) fluidly connected to the flexible, impermeable tube (103). In this embodiment, the pressure source (102) is a cardiovascular pump. The upstream segment (119) contains the working fluid for the cardiovascular pump, in this embodiment, water. The downstream segment (129) and the flexible tube (103) contain the experimental medium (107). Surrounding a portion of the flexible tube (103) is an AGB (101). Downstream of the AGB is an outlet container (108) to contain used experimental medium (107). In this embodiment, the pressure measurement system comprises an access port (111), a Huber needle (110) and a pressure gauge (105). The access port (111) is fluidly connected to the AGB (101) via connection tube (112), and allows access by the Huber needle (110) to the interior of the AGB (101) so that the pressure inside the AGB (101) can be measured. The Huber needle transmits the pressure to the pressure gauge (105). The pressure gauge (105) is connected via a USB cable (106) or other suitable connector to a data processor (113), preferably a PC. In this embodiment, the AGB (101) is pressurized by the water column (906) which is a water tube connected through a cock valve (910) to the pressure gauge cavity. The cock valve (910) must be closed before the bolus is generated in order to ensure that the pressure inside the AGB (101) is affected only by the bolus of food. The method used to achieve this initial pressure is by the height of the water column $\Delta h$ (920). As described hereinabove, the AGB (101) and the pressure gauge (105) are placed at the same elevation. The water in the water column will then cause a pressure in the AGB. If, for a non-limiting example, the height $\Delta h$ (920) is $\Delta h=580\pm1$ mmH$_2$O, then the gauge pressure in the AGB will be $\Delta P=42.6\pm0.07$ mmHg. In $\Delta h=580\pm1[\text{mmH}_2\text{O}] \rightarrow \Delta P=42.6\pm0.07$ [mmHg] general, the standard AGB initial pressure can vary from 40 to 80 mmHg.

Each experiment was repeated more than 30 times (about 50-60 times) on each medium for statistical reasons while relying on (*Guidance for the Use of Bayesian Statistics in Medical Device Clinical Trials, Food And Drug Administration*; Feb. 5, 2010). According to this document, sampling 29 signals gives a 95% confidence level; sampling even more signals gives a greater confidence level.

The pressure inside the AGB (101) will vary between experiments as a result of its physical size, about 12 [mm] stoma diameter. Due to the accuracy of measurement of the height of the water column and due to physical differences, such as, for example, wrinkles in the flexible tube (103), the AGB pressure is accurate to within ±0.88 [mmHg]. As this will occur in vivo, it is not otherwise accounted for in this Example.

Figure 7:
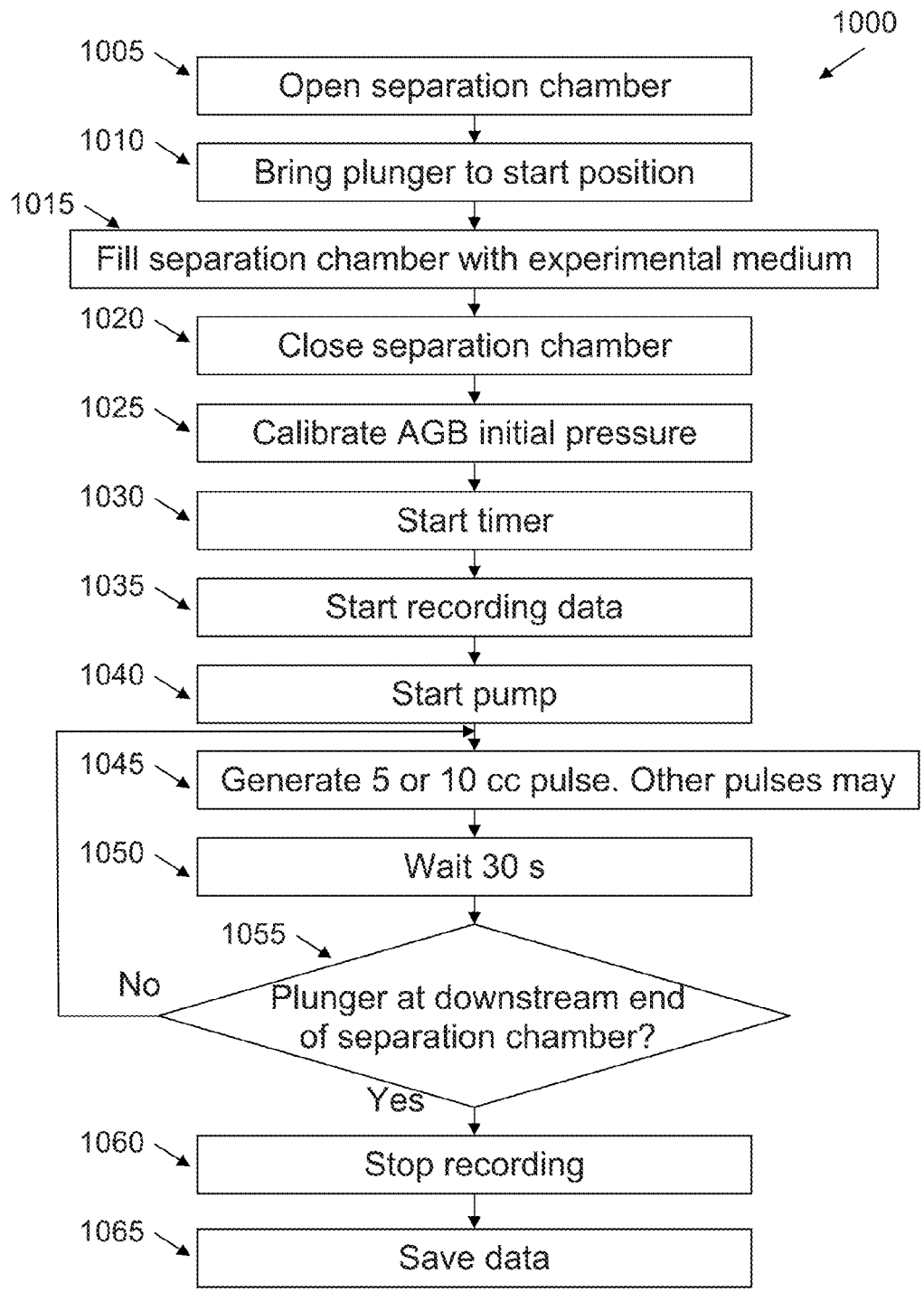
FIG. 7 schematically illustrates a flow chart of the operation of an embodiment of the system of the present invention.

In reference to FIG. 7, the experimental protocol for a set of experiments is as follows:
Open the separation chamber (109) (1005).
Bring the plunger (104) to start position (1010).
Fill the separation chamber (109) with desired experimental medium (107) (A, B or C) (1015).
Close the separation chamber (109) (1020).
Calibrate AGB pressure to initial pressure, about 40[mmHg] (1025).
Start the timer (1030).
Start recording data with National Instruments GUI (1035).
Start the Cardio Vascular Pump (1040).
Generate a 5 or 10 cc pulse (1045) then wait 30 seconds (1050). 30 s is the average time between bites in a meal. In other embodiments, other pulse volumes are used.
Repeat last line until the plunger reaches the end of the separation chamber (1055).
Stop recording (1060) and save Data to a MS Excel file (1065).

This set of instruction is repeated as many times as necessary.

EXAMPLE 2

Example 2 is am embodiment of the analysis of the data collected in Example 1.

The analytical method is based on one developed by Castell (Donald O. Castell, Computer-Aided Analysis of Human Esophageal Peristalsis). In it, Castell showed that a computer can perform analysis of pressure data acquired during passage of a bolus of food through a constriction such as an AGB, by determining the wave amplitude, duration, average upward slope (dP/dT), velocity of wave progression, area under each wave and maximum upward slope (Max dP/dT). However, in this embodiment, the pressure data for passage of a single bolus of food through an AGB (a signal) are characterized by 3 characteristics: peak or maximum pressure in each signal, area under the signal and fading rate factor.

The data files generated by the experiments described in Example 1 were stored as MS Excel files of voltage vs. time. Since the sampling rate was 50 Hz and the duration of the passage of each bolus of food (each experiment) was 30 s, each signal consisted of 1500 data. For non-limiting example, data analysis can be made using a MATLAB program or similar software.

Figure 8:
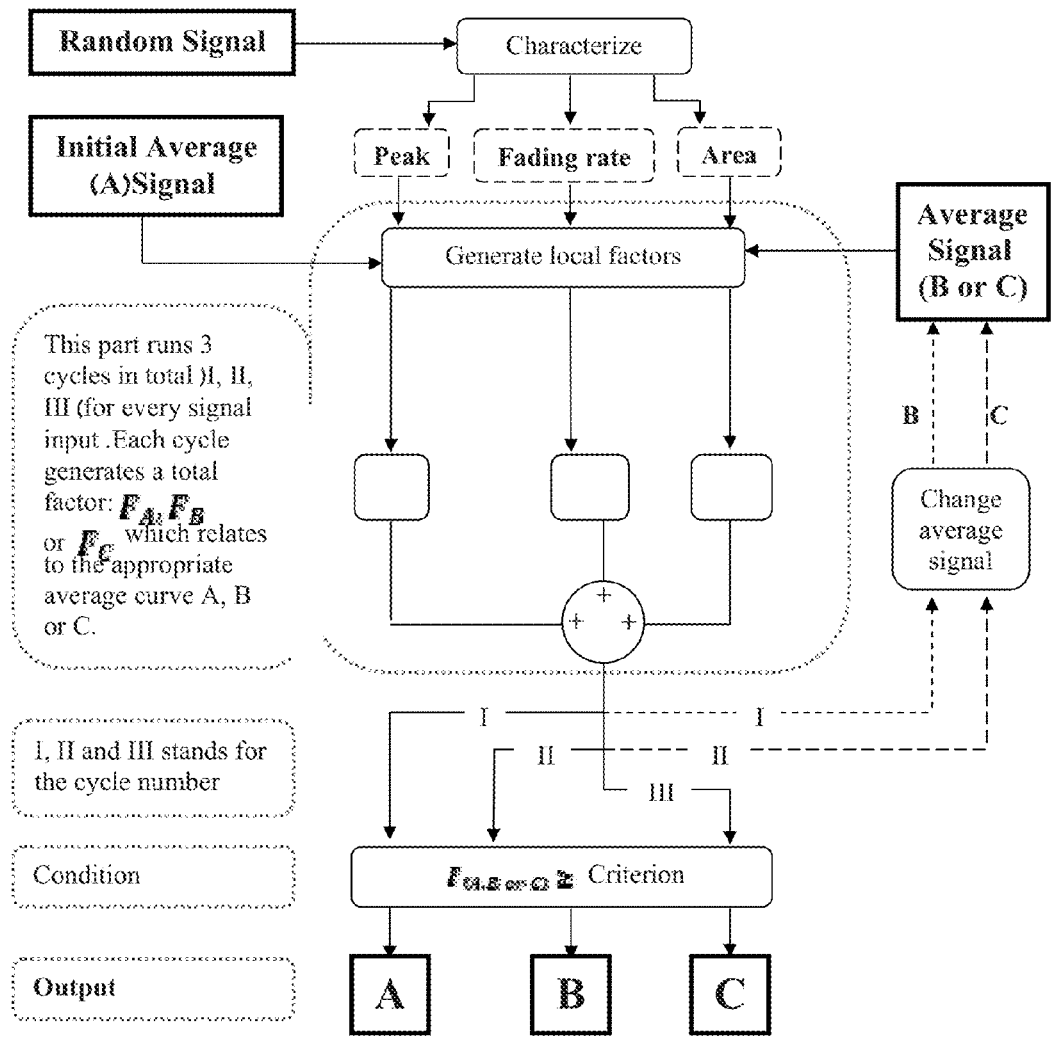
FIG. 8 schematically illustrates a method of determining the identifying factors $F_A$, $F_B$, and $F_C$.

In reference to FIG. 8, a schematic is shown of an embodiment of an algorithm for an analysis process for a signal. This algorithm gets a random signal input and gives the most suitable outputs, A, B and/or C. Clustering the random signals into 3 groups (A, B and C) is made by the disassembly of the signal into three parameters: peak, Area and fading rate. The logical principle behind this algorithm relies on producing a quantification factor for each signal related to the 3 references average signals, this factor is the "total factor" parameter which can have any value between 0 and 1, while as closer to 1 the factor is, closer to the reference average the scanned signal is.

The total factors are used to define whether a given signal was produced by a food of type A, type B or type C, as described hereinbelow. Total factors $F_A$, $F_B$ and $F_C$ are between 0 and 1, so that (0≤Total factor≤1) and are generated using the equation:

$$\text{Total factor} = g_1 \cdot F_{Peak} + g_2 \cdot F_{Area} + g_3 \cdot F_{Fade},$$

where the $g_i$ are gain factors and the $F_i$ are local factors. All the components of equation (3) are explained hereinbelow.

These total factors are the final factor used by the algorithm to "decide" the proper output.

The local factors $F_{Peak}$, $F_{Area}$, and $F_{Fade}$ are between 0 and 1, so that (0≤local factor≤1). Each local factor represents the approximation of the scanned signal to the average curve in terms of Peak, Area and Fading rate. They are generated as follows:

The peak factor is:

$$\text{Peak factor} \rightarrow F_{Peak} = 1 - \frac{|\text{Peak} - \text{average Peak}|}{\frac{\sigma_{Peak}}{2}} \quad (4)$$

The area factor is:

$$\text{Area factor} \rightarrow F_{Area} = 1 - \frac{|\text{Area} - \text{average Area}|}{\frac{F_{Area}}{2}} \quad (5)$$

and the fading factor is $$\text{Fading factor} \rightarrow F_{Fade} = 1 - \frac{1}{10} \frac{\sum_{j}^{i}[\text{Pressure} - \text{Average Pressure}]}{[j-i]} \quad (6)$$

where

Peak, Area and Pressure relate to the actual value of the peak, area and pressure extracted from the scanned signal.

Figure 11:
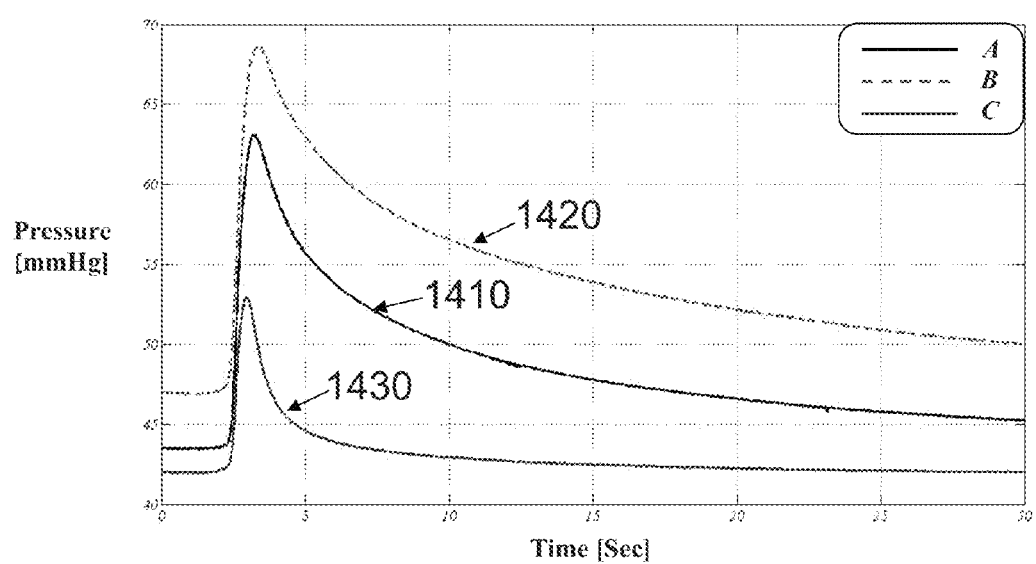
FIG. 11 schematically illustrates average signals for three different consistencies of food.

Average Peak, average Area and average Pressure relates to the average values (Extracted from the average curves, FIG. 11).

Figure 12:
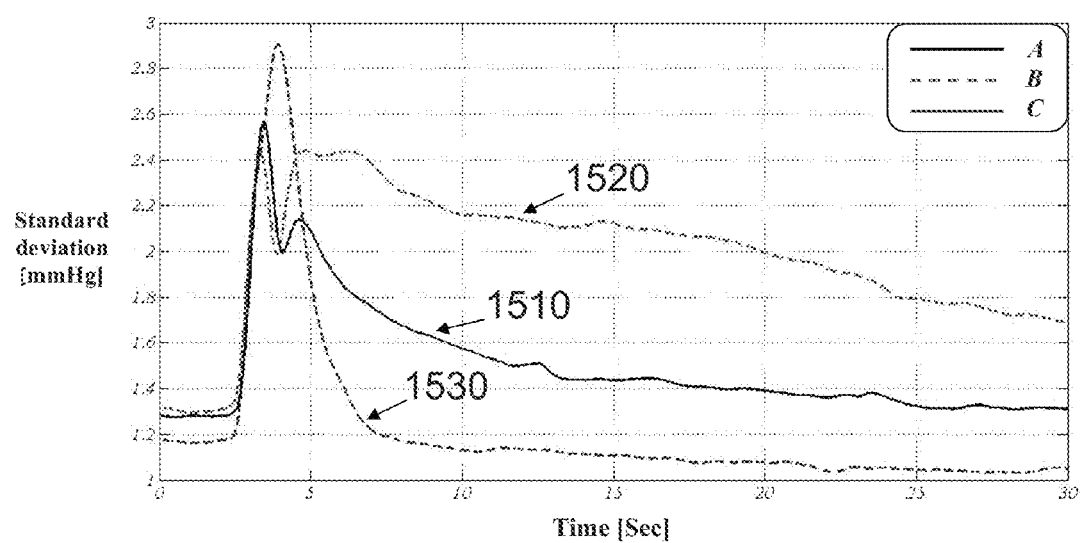
FIG. 12 schematically illustrates the standard deviations of the average signals for three different consistencies of food.

$\sigma_{Peak}$: Is the peak standard deviation value, extracted from the standard deviation analysis (FIG. 12).

$\sigma_{Area}$: Is the Area standard deviation, this value is calculated particularly for the algorithm usage.

$$\left(\sigma_{Area_A}=1972;\ \sigma_{Area_B}=2738;\ \sigma_{Area_C}=1599;\ \left[\frac{\text{kg}}{\text{m}\cdot\text{sec}}\right]\right)$$

i=Special point time coordinate; (the method of determining i is described hereinbelow)

j=End of Signal time coordinate

The gain coefficients $g_1$, $g_2$, and $g_3$ are weighting factors. In all embodiments, $(0 \leq g_1, g_2, g_3 \leq 1)$ and $g_1 + g_2 + g_3 = 1$. \quad (7)

In this embodiment, $(0 \leq g_1, g_2, g_3 \leq 1)$ $g_1 = g_2 = g_3 = 1/3$ so that each local factor contributes an equal portion to the total factor. In other embodiments, different values of $g_1$, $g_2$, and $g_3$ are used, subject to the constraints in equation (7).

Figure 9:
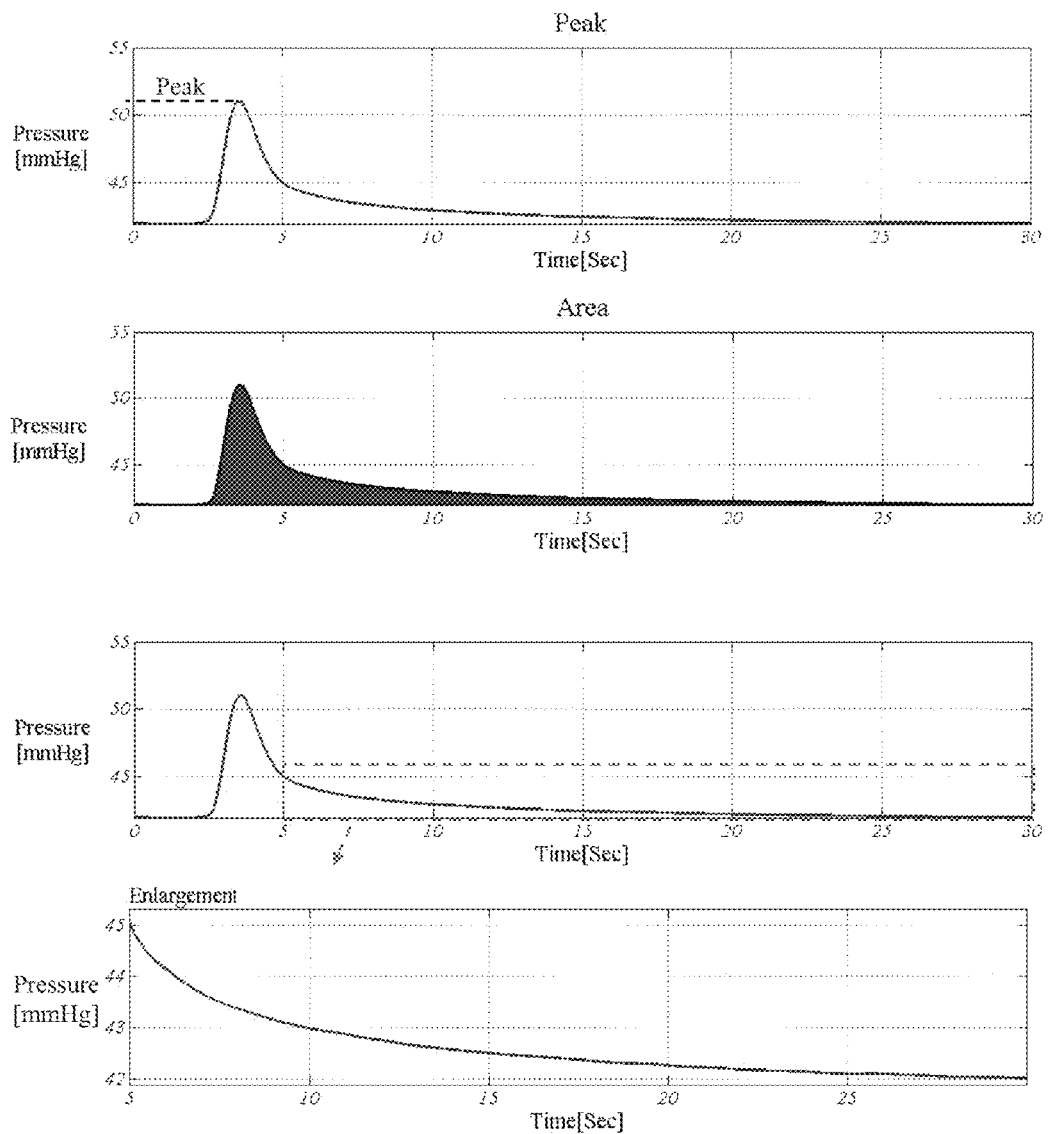
FIG. 9 schematically illustrates how the characteristics of the signals are determined.

In reference to FIG. 9, signals are characterized, as described hereinabove, in terms of three factors. FIG. 9 shows a typical signal. In FIG. 9A, the peak as used herein, the maximum pressure in the signal, is marked by a dashed line. In FIG. 9B, the area as used herein, the total area under the signal (in kg m$^{-1}$ s$^{-1}$) is shown by the grey under the curve. FIG. 9C and FIG. 9D show the part of the signal used to determine the fading rate. In FIG. 9C, the fading rate is determined during the time indicated by the dashed lines, in this example, from 5 s to 30 s. FIG. 9D shows an enlargement of this part of the signal curve.

Figure 10:
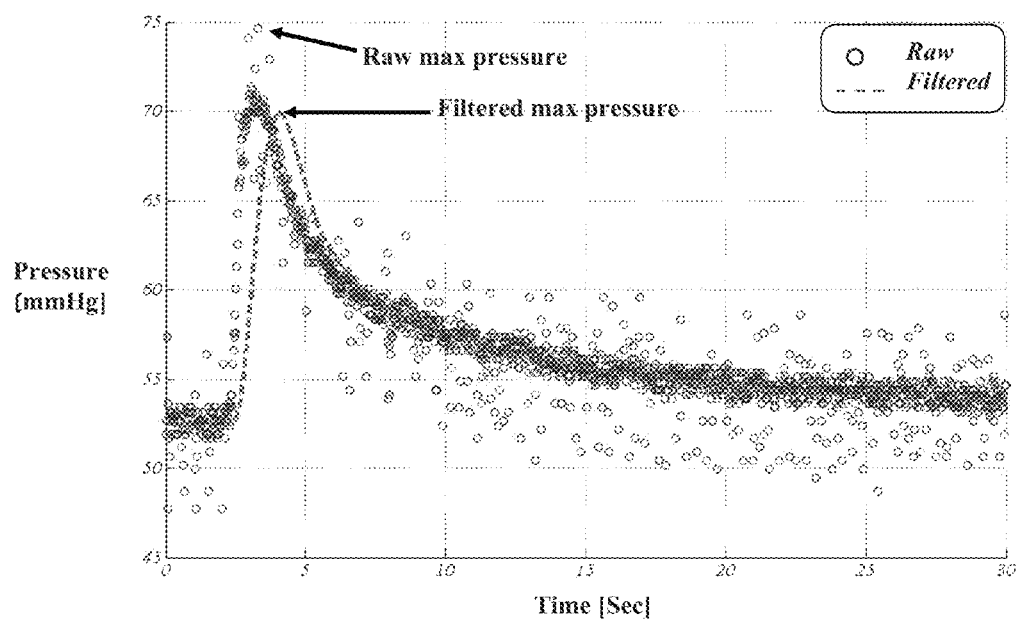
FIG. 10 schematically illustrates the effect of filtering on the signal.

In reference to FIG. 10, the effect of filtering is shown for a typical signal. In FIG. 10, the circles show the raw data, while the line shows the filtered data. Filtering is critical for retrieving data from the signals. Since there is noise in the electronic system, as can clearly be seen in FIG. 10, retrieving data from the raw signal can be misleading. For example, the maximum pressure value is ~75[mmHg] for the raw data and ~70[mmHg] for the filtered data, about a 7% difference between the raw and filtered values. Filtering, however, also has a negative effect on the data. For example, in FIG. 10 there is about 1 second difference between the time the maximum pressure occurs, according to the raw data and the time the maximum pressure occurs, according to the filtered data. Since this time is not critical for the analysis and the distortion is the same for all the signals, it will not significantly affect the results.

Use of a filter is very important for another reason, related to analysis of the standard deviation. Because of the presence of noise in the raw signal, as seen in FIG. 10, the standard deviation of the average of raw signals will be significantly greater than the standard deviation of the average of the filtered signals.

The filter that was used in this analysis is a Butterworth Low Pass Filter with the cutoff frequency set to $\omega_C$=0.5 [hz], the frequency of data acquisition. As a non limiting example, any other filtering system capable of achieving the same may be used. Also, different calibrations may be used.

In general, the Butterworth Low Pass Filter conditions the signal via the equation $$G_{(\omega)} = \frac{G_0}{\sqrt{1+\left(\frac{\omega}{\omega_c}\right)^{2n}}}, \quad (8)$$

where:
$G_{(\omega)}$=Gain in ($\omega$)frequency
$G_0$=Gain in (0)frequency
$\omega_c$=Cuttoff frequency
$\omega$=2πf, angular frequency
n=Order of filter In this embodiment
$G_0$=1, no gain was added
n=2, and $$\omega_c = 2\pi \cdot \frac{1}{2}\left[\frac{\text{rad}}{\text{sec}}\right], f = \frac{1}{2}[\text{hz}]$$

For this example, the order n of the filter was set empirically. Inserting the above values for $G_0$, n and $\omega_c$ into equation (8), the filtering factor G becomes $$G = \frac{G_0}{\sqrt{1+\left(\frac{\omega}{\omega_0}\right)^m}}$$

$$= \frac{1}{\sqrt{1+\left(\frac{2\pi f}{2\pi \cdot \frac{1}{2}}\right)^4}}$$

$$G = \frac{1}{\sqrt{1+(2f)^4}}$$

In this example, the sampling frequency is 50[Hz], electronic noise caused by the net in Israel is also 50[Hz].

Applying a low pass filter with a cutoff frequency of ½[Hz] ensures the disappearance of the 50[Hz] noise and the passage of the main experiment frequency which is 1/30[Hz]. note: (1/30<½<50)

In reference to FIG. 11, the middle curve (1410) represents the average signal for medium A, the upper curve (1420) represents the average signal for medium B, and the lower curve (1430) represents the average signal for medium C. These curves are used as "models" by the algorithm.

In reference to FIG. 12, the middle curve (1510) represents the standard deviation of the average signal for medium A, the upper curve (1520) represents the standard deviation of the average signal for medium B, and the lower curve (1530) represents the standard deviation of the average signal for medium C. The standard deviation of the peak, as discussed hereinbelow, is derived from these curves.

In this example, the data are normalized by dividing each value in a signal by the maximum pressure in that signal, such that the normalized signal is $$\frac{p}{p_{max}}.$$

Figure 13:
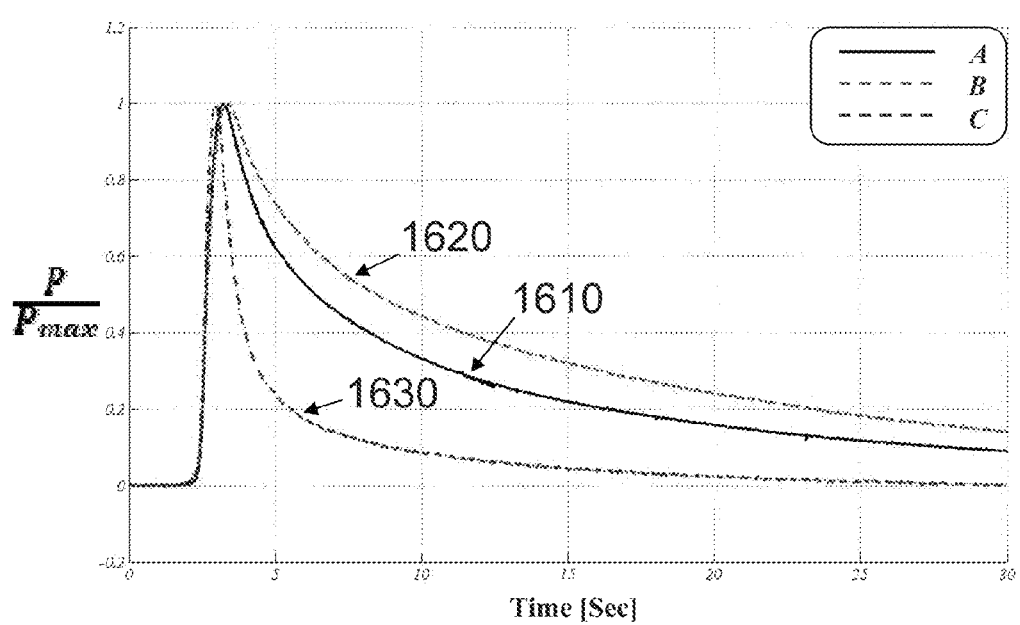
FIG. 13 schematically illustrates normalized signals for three different consistencies of food.

In reference to FIG. 13, middle curve (1610) represents the normalized signal derived from the average signal for medium A, the upper curve (1620) represents the normalized signal derived from the average signal for medium B, and the lower curve (1630) represents the normalized signal derived from the average signal for medium C. In this example, the composition ratios for the three media are:

$$A \to \frac{1}{10}\frac{Granulate}{liquid}; B \to \frac{1}{5}\frac{Granulate}{liquid}; C \to \frac{1}{15}\frac{Granulate}{liquid}$$

The curve shapes are as expected, in that the more liquid the experimental medium contains, the faster the pressure returns to its initial value. As a non limiting example, the protocol used for providing said media consists of boiling for 20 minutes 1 part rice, as granulate, with 5, 10, and 15 parts water, in closed container. After 20 minutes, the medium was left to reach 37° C. Of course, other ingredients may be used, in order to imitate different food consistencies. Assuming that the standard meal is under the supervision of a clinician, more than 3 graphs may be determined, allowing a specific calibration to a specific patient.

It is necessary to determine the time point at which to begin the fading rate analysis (referred to as i hereinabove). This point cannot be before the peak because, during this stage, the pressure is still going up and we want the pressure fading rate i.e. the rate at which the pressure goes down, so the point has to be after the peak and before the end of the signal. The "special point" is expected to be an intersection point between different pressure regimes.

Figure 14:
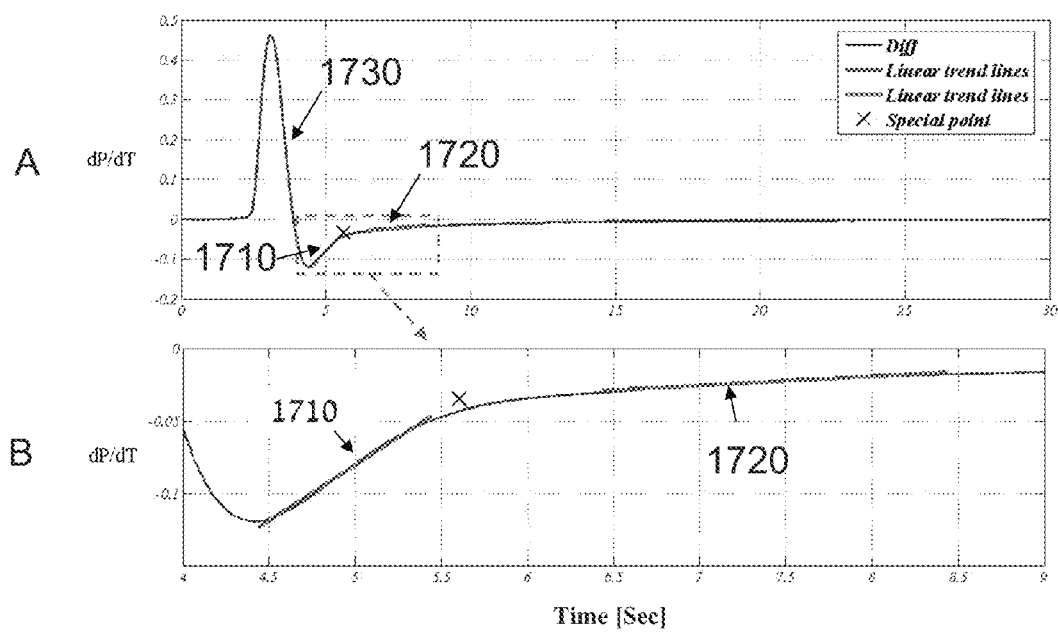
FIG. 14 schematically illustrates the time differential of the normalized signals for three different consistencies of food.

In reference to FIG. 14, FIG. 14A shows a typical first derivative of the normalized pressure signal (1730). The derivative reaches a peak, falls to a minimum, at a time, in this example, of approximately 4.5 seconds, and, in this example, has nearly reached zero (the pressure is approximately constant) by a time of approximately 13 s. During the time period between approximately 4.5 s and approximately 10 s, there are two regions of the curve where it is approximately linear (1710 and 1720) and where the slopes are significantly different. The time period from 4 to 9 seconds, shown by the dotted lines in FIG. 14A, is expanded in FIG. 14B to shown these two regions more clearly. The special point, marking the time at which measurement of the "fading rate" starts, is the point where the two lines 1710 and 1720 intersect. It is marked by an X in FIG. 14B. In this example, for this signal, the special point marks a time of approximately 5.6 s. The intersection point analysis is applied to the first order derivative for each average curve (A, B and C), therefore 3 intersection points are generated in total.

Figure 15A:
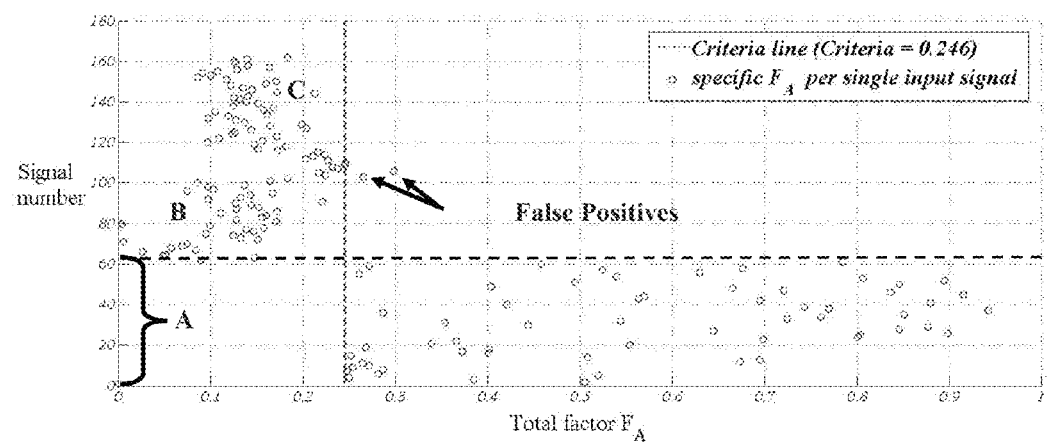
FIG. 15 schematically illustrates values for the identifying factors $F_A$, $F_B$, and $F_C$ for randomly selected boluses of food.

In reference to FIG. 15, FIG. 15A represents the $F_A$ factor for a given random signal. Each blue circle is an $F_A$ factor, the algorithm clusters blue circle to the right of the vertical dashed criterion line ($F_A$=0.246) as "A" signal, we see that if we move the criterion line lower (0.2 for example) we will recognize all the "A" signals as "A" signals but at the same time some B and C signals will be added to the A recognitions which means lower confidence level because of the presence of more false positive and, as explained hereinbelow, in this case fewer false positives means better results even if more false negatives are present.

Figure 15B:
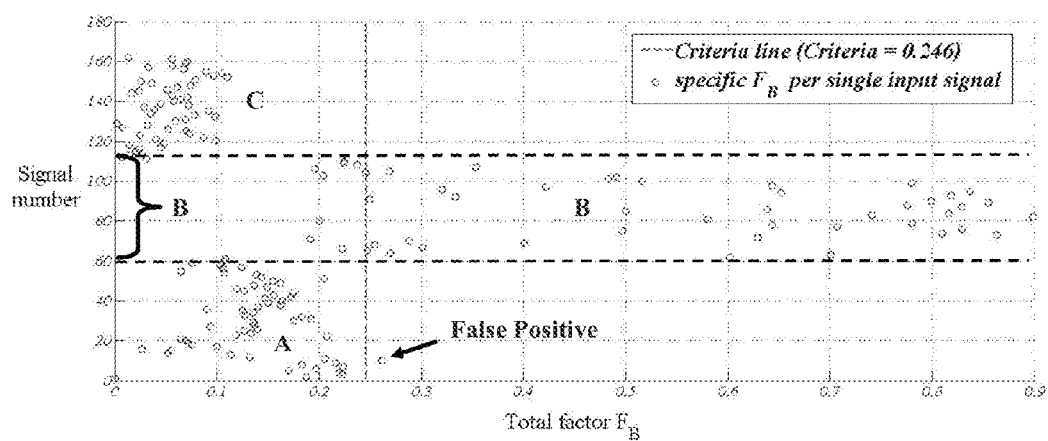
Figure 15C:
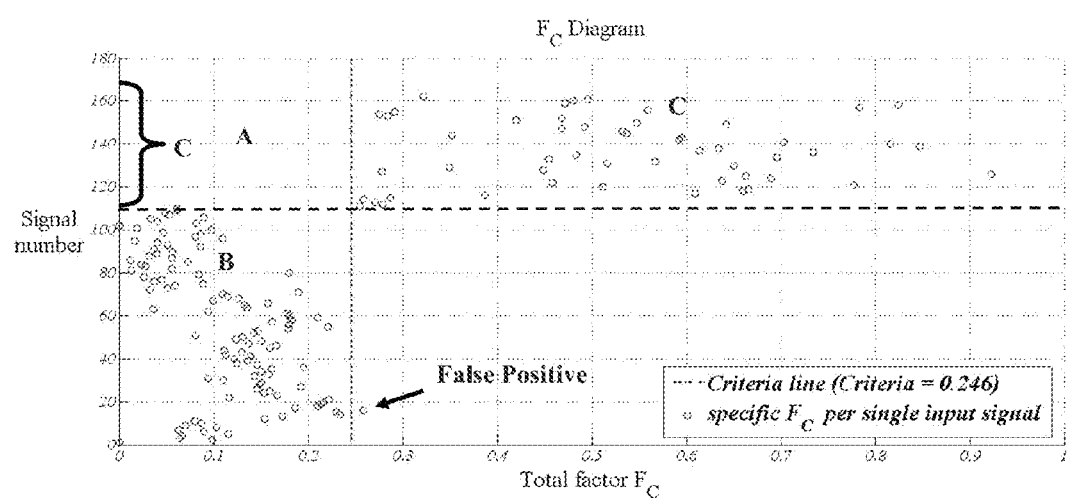

Similarly, FIGS. 15B and 15C represent the $F_B$ and $F_C$ total factors for a given random signal. Each circle is a total factor. It can be clearly seen that the algorithm clusters circles to the right of the criterion line as "B" or "C" signals, respectively.

Table 2 shows the algorithm's success rate in food type recognition. It is clear that the more liquid in the medium, the better the success rate, while more granulated mediums have a lower success rate. The smallest success rate (81.6%), for medium B, is still greater than 80%, which is acceptable for analysis of eating patterns. The reason for this phenomenon and reference to the percentage will be discussed hereinbelow.

TABLE 2

| | Algorithm results | | | |
|---|---|---|---|---|
| Medium | Total signals | Identified signals | False positive | Success rate[%] |
| A | 60 | 60 | 2 | 100 |
| B | 49 | 40 | 1 | 81.6 |
| C | 52 | 52 | 1 | 100 |

These algorithm results are exemplary, based on bench-testing an in vitro system. Of course, the system and method is tailored to the individual patient, with, where necessary, more than the three exemplary representations described herein of liquid, semi liquid and solid food. Combining results from more types of food using such a system and method will improve results.

Figure 16:
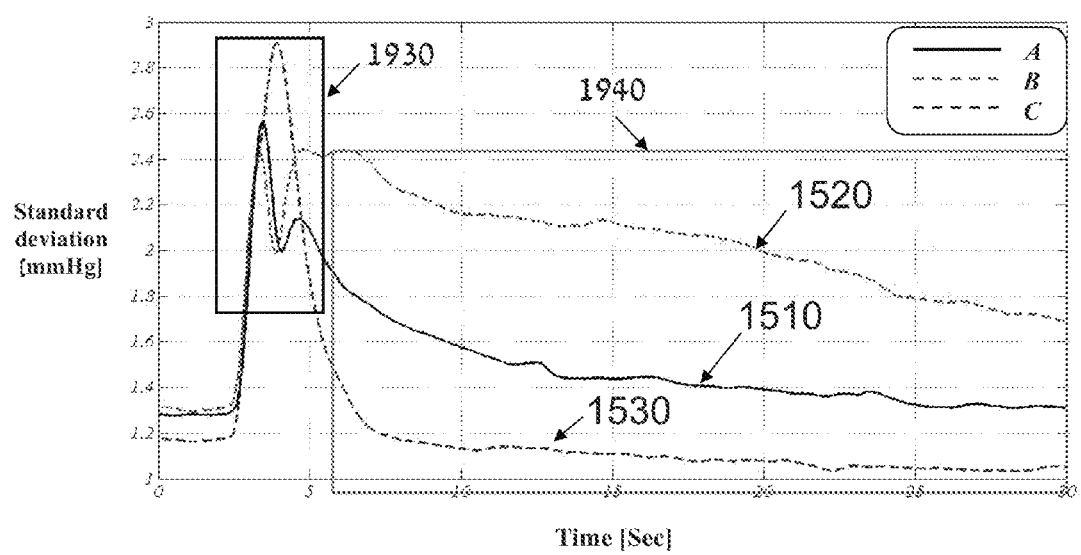
FIG. 16 schematically illustrates the standard deviations of the average signals for three different consistencies of food.

In reference to FIG. 16 which shows the same first derivative of pressure vs. time curves as FIG. 12, there are two time regimes, one containing the peak pressure (1930) on the left, including the peak of the pressure and the peak of the rate of change of pressure. The second, (1940), on the right, includes the fading rate region. In all of the second region (1940), the standard deviation of medium "C" (1530), with the highest liquid percentage, is the smallest. In all of the second region (1940), medium "A" (1510) has higher standard deviation values than medium "C" (1510) but less than medium "B" (1520) and medium "B" (1520), the most granular medium, has the highest standard deviation values after the peak. There is a clear relation between granularity and standard deviation in the fading rate region (1940); more granularity brings a higher standard deviation while more liquid brings a lower standard deviation.

In further reference to FIG. 16, the standard deviation in the peak area (1930) reveals a behavior in which we see an inverse relation between medium granularity and peak (maximum pressure) standard deviation values, i.e. more granularity brings lower standard deviation values while more liquid brings higher standard deviation values.

Figure 17:
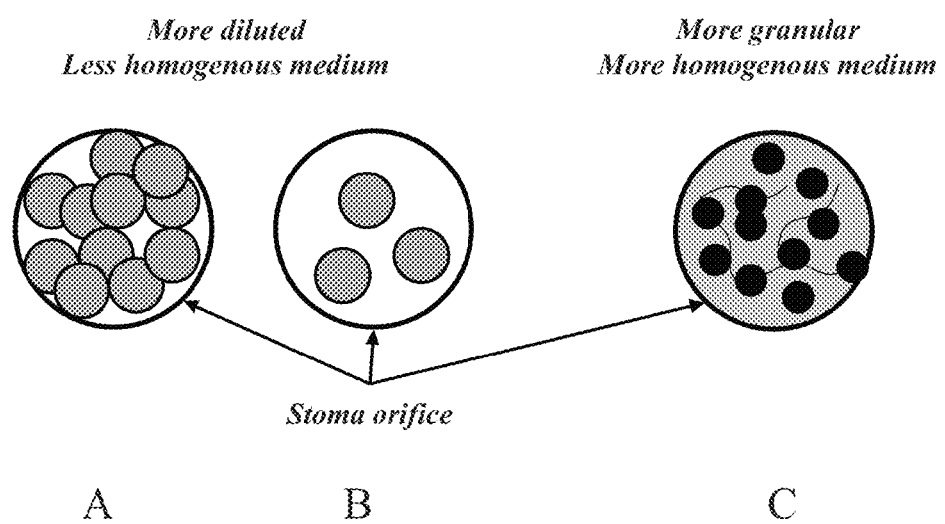
FIG. 17 schematically illustrates the effect of random variation on the granularity of different types of food.

As shown hereinabove, there is a contrast between the peak standard deviation and the fading rate standard deviation behaviors related to granularity properties of the medium, with the peak standard deviation behavior opposite to that of the fading rate standard deviation with respect to medium granularity. A medium containing more liquid can be less homogeneous than a medium containing less liquid. A good example for this is a soup with croutons. Each bolus—each spoonful of soup—might contain more or fewer croutons depending on the spoon position when leaving the soup bowl while picking up floating croutons. If the soup contains many croutons (the medium contains less liquid), each spoonful will be covered with croutons and the number of croutons per spoonful (the amount of solid per bolus) will be approximately constant. If the soup contains few croutons (the medium contains more liquid), different spoonfuls—different boluses—will have different number of croutons (different amounts of solid). Moreover, high water content food with rapidly separating granules may lead to a plug flow, where the granules separate the medium and accumulate and restrict the orifice size. On the other hand, oatmeal is much thicker and denser and contains more granular particles, yet due to its ability to hold a relatively stable dispersion, this hydrocolloid system is more homogenous. These examples demonstrate a major medium character, "uniformity" or "homogeneity", and we see a relation between homogeneity and granularity vs. dilution. A schematic visualization of this phenomenon shown in FIG. 17. In FIGS. 17A and 17B differences between boluses are illustrated, with the bolus of FIG. 17A having more granular matter than the bolus in FIG. 17B. FIG. 17C illustrates a more homogenous medium. Peak standard deviation behavior relates to maximum pressure which is very sensitive to a non-homogenous medium because the maximum (peak) pressure is developed when the bolus passes through the stoma. For example, the maximum pressure would be larger for the bolus shown in FIG. 17A than for the bolus shown in FIG. 17B because the particles of FIG. 17A by chance form a stopper which prevents the continuous passage of food, or, in other words, causes a plug flow.

On the other hand, the fading rate standard deviation relates to the conversion of potential energy stored in the small pouch simulator to the kinetic energy of the medium, since during the fading time frame no external energy is supplied to the system. And, since more diluted mediums show less motion resistance, they tend to absorb the potential energy faster than more granular mediums, which means getting more quickly back to their initial values which, in turn, leads to lower fading standard deviation.

The algorithm of Example 2 can be applied to monitor the eating behavior of a living patient. A meal can be defined as at least a few bites (boluses of food). For a non-limiting example, a "meal" is defined as at least 10 bites within a given time, with fewer than 10 bites within the same timeframe being defined as a "snack". The patient is eating an exemplary meal, such as a hamburger. For the purposes of the example, the food's characteristics are close to those of "Medium B" after chewing. According to the algorithm empirical results, more than 80% of the bites or boluses can be identified, so, in this example of a minimal meal consisting of 10 bites, 8 boluses out of the 10 total bites can be recognized, which is clearly enough to determine the consumed food type granularity and the duration of the meal. Multiplying by the average bolus size will also indicate the total amount of consumed food. The bolus of food is averaged for a patient, since patients eat almost consistent volumes of bolus. Boluses vary between patients, ranging from 1 to 50 cc, most commonly between 5 and 15 cc. Calibrating the measured volume for a specific patient allows indication of the amount of food consumed, by multiplying number of boluses by the average bolus volume. This data may be used either to determine the weight of food eaten or, when the patient is provided with known weight standard meal, an indication of bolus volume can be found.

Using the algorithm derived above, a new calibration protocol based on pressure collected data can be derived and the calibration can be amended in accordance with the patient's current eating patterns to reduce vomiting and to improve the patient's eating behavior by, for non-limiting example, enabling the patient to recognize that food is not being chewed sufficiently, or that bites are too large, or that too much is being eaten. Recording of such data will enable the clinician to observe the patient's eating behavior and to assist the patient to avoid eating behaviors likely to have unfavorable outcome.

Behavior which is observable using the algorithms described herein: What type of food is the patient consuming? How many meals the patient has per day? Is the patient chewing his food enough? Were there vomiting events following the calibration? After recalibrating, is the current stoma adjusted to the patient's need? What are meal durations? What are the intervals between each bite and do they correspond with the pouch emptying time? Is the patient a fast eater? Is the patient a night eater and what kind of food? Does the patient drink during the meal? Is there a change in the patient's pressure regime since the last calibration? (This may indicate the development of a problem with the AGB or within the patient's body).

The present invention provides a system for modifying the eating behavior of a patient equipped with a gastric restriction apparatus comprising:
  a. at least one adjustable gastric band (AGB);
  b. at least one pressure sensor to measure pressure within said AGB;
  c. at least one processing unit in communication with said pressure sensor, said processing unit containing instructions to collect at least one set of at least one pressure measurement and to analyze said at least one set of at least one pressure measurement;
  d. at least one data base comprising data concerning pressure exerted within said AGB by a bolus of liquid food, a bolus of semiliquid food, and a bolus of solid food;
  e. at least one means of recording said pressure measurements;
  f. at least one means of recording the results of said analysis; and
  g. at least one means of using said distinction of said current eating pattern to modify said eating behavior of said patient.

The present invention further provides a method for modifying the eating behavior of a patient equipped with a gastric restriction apparatus (GRA) comprising steps of:
  a. providing an adjustable gastric band (AGB);
  b. providing a pressure sensor to measure pressure within said AGB;
  c. providing a processing unit in communication with said pressure sensor, said processing unit containing instructions to collect at least one set of at least one pressure measurement and to analyze said at least one set of at least one pressure measurement;

d. providing a data base comprising data concerning pressure exerted within said AGB by a bolus of liquid food, a bolus of semiliquid food, and a bolus of solid food;

e. providing a means of recording said sets of at least one pressure measurements;

f. providing a means of recording the results of said analysis;

g. providing a means of communicating said results to at least one of a group consisting of a patient, a clinician, a doctor, a nurse, a dietician, and a researcher;

h. placing said AGB in position, said AGB at least partially surrounding a stoma orifice near the upper end of the stomach;

i. measuring said pressure within said AGB as said bolus of food passes through said stoma orifice;

j. analyzing said measured pressure; and, k. using said distinction of said current eating pattern to modify said eating behavior of said patient.

It is another object of the present invention to disclose a method for determining the consistency of food entering the stomach comprising steps of:

a. providing an adjustable gastric band (AGB);

b. providing a pressure sensor to measure pressure within said AGB;

c. providing a processing unit in communication with said pressure sensor, said processing unit containing instructions to collect at least one set of at least one pressure measurement and to analyze said at least one set of at least one pressure measurement;

d. providing a data base comprising data concerning pressure exerted within said AGB by a bolus of liquid food, a bolus of semiliquid food, and a bolus of solid food;

e. providing a means of recording said sets of at least one pressure measurements;

f. providing a means of recording the results of said analysis;

g. providing a means of transmitting said results to at least one of a group consisting of a patient, a clinician, a doctor, a nurse, a dietician, and a researcher;

h. placing said AGB in position, said AGB at least partially surrounding a stoma orifice near the upper end of the stomach;

i. measuring said pressure within said AGB as said bolus of food passes through said stoma orifice; analyzing said measured pressure; and k. transmitting said results to at least one of a group consisting of a patient, a clinician, a doctor, a nurse, a dietician, and a researcher thereby distinguishing between at least two of a group consisting of liquid food, semiliquid food, and solid food.

It is another object of the present invention to disclose the method for determining the consistency of food entering the stomach, additionally comprising a step of transmitting at least one of a group consisting of at least one of said least one set of at least one pressure measurement and said results to a location remote from said patient.

It is another object of the present invention to disclose the method for determining the consistency of food entering the stomach, additionally comprising a step of adapting the system alter itself in response to changes in at least one of a group consisting of food consistency, food granularity, bolus size, and duration of eating.

It is another object of the present invention to disclose the method for determining the consistency of food entering the stomach, additionally comprising a step of providing said bolus of liquid food comprising a standard formulation, said bolus of semiliquid food comprising of a standard formulation, and a bolus of solid food comprising a standard formulation.

It is another object of the present invention to disclose the method for determining the consistency of food entering the stomach, additionally comprising a step of providing a database of results of analyses of a plurality of sets of at least one pressure measurement of at least one bolus of liquid food, at least one bolus of semiliquid food, and at least one bolus of solid food.

It is another object of the present invention to disclose the method for determining the consistency of food entering the stomach, additionally comprising a step of making said distinction on the basis of a total factor, said total factor defined as Total factor $=g_1 \cdot F_{Peak} + g_2 \cdot F_{Area} + g_3 \cdot F_{Fade}$, said $g_i$ being weighting factors and said $F_i$ being local factors.

It is another object of the present invention to disclose the method for determining the consistency of food entering the stomach, additionally comprising a step of calculating said total factor three times for each said bolus of food, once on the assumption that said food has the consistency of said liquid food, once on the assumption that said food has the consistency of said semiliquid food, and once on the assumption that said food has the consistency of said solid food.

It is another object of the present invention to disclose the method for determining the consistency of food entering the stomach, additionally comprising a step of limiting said weighting factors $g_i$ to be greater than or equal to zero and less than or equal to 1.

It is another object of the present invention to disclose the method for determining the consistency of food entering the stomach, additionally comprising a step of deriving said local factors $F_{peak}$, $F_{Area}$ and $F_{Fade}$ from said at least one set of at least one pressure measurement.

It is another object of the present invention to disclose the method for determining the consistency of food entering the stomach, additionally comprising a step of limiting said local factors $F_{Peak}$, $F_{Area}$ and $F_{Fade}$ to be greater than or equal to zero and less than or equal to 1.

It is another object of the present invention to disclose the method for determining the consistency of food entering the stomach, additionally comprising a step of calculating said local factor $F_{Peak}$ from $$F_{Peak} = 1 - \frac{|\text{Peak} - \text{average Peak}|}{\frac{\sigma_{peak}}{2}},$$

Peak is the maximum pressure in one set of at least one pressure measurement, average Peak is the average maximum pressure of a plurality of sets of at least one pressure measurement, and $\sigma_{Peak}$ is the standard deviation of the average maximum pressure of a plurality of sets of at least one pressure measurement.

It is another object of the present invention to disclose the method for determining the consistency of food entering the stomach, additionally comprising a step of calculating said local factor $F_{Area}$ from $$F_{Area} = 1 - \frac{|Area - \text{average Area}|}{\frac{\sigma_{Area}}{2}},$$

Area is the area under the curve of pressure vs. time generated from the at least one set of at least one pressure measurement, average Area is the average area under the curve of pressure vs. time generated from a plurality of sets of at least one pressure measurement, and $\sigma_{Area}$ is the standard deviation of the average area under the curve of pressure vs. time generated from a plurality of sets of at least one pressure measurement.

It is another object of the present invention to disclose the method for determining the consistency of food entering the stomach, additionally comprising a step of calculating said local factor $F_{Fade}$ from $$F_{Fade} = 1 - \frac{1}{10} \frac{\sum_{j}^{i} [Pressure - \text{average Pressure}]}{j - i},$$

Pressure is pressure measurement at a time during the measurement of the at least one set of at least one pressure measurement, average Pressure is the average of pressure measurements at that time generated from a plurality of sets of at least one pressure measurement, j is the start time for the time period, and i is the end time for the time period.

It is another object of the present invention to disclose the method for determining the consistency of food entering the stomach, additionally comprising a step of selecting the start of said time period to be after the time at which the peak pressure occurs.

It is another object of the present invention to disclose the method for determining the consistency of food entering the stomach, additionally comprising a step of selecting the start of said time period to be after the time at which there is a minimum in the rate of change of pressure as a function of time.

It is another object of the present invention to disclose the method for determining the consistency of food entering the stomach, additionally comprising a step of selecting the start of said time period to be at a special point.

It is another object of the present invention to disclose the method for determining the consistency of food entering the stomach, additionally comprising a step of selecting said special point to be the intersection of the lines defining the slopes of two regions of approximately constant slope in the plot of rate of change of pressure as a function of time, said regions being after the minimum of the plot of rate of change of pressure as a function of time, said approximately constant slopes different from each other.

It is another object of the present invention to disclose the method for determining the consistency of food entering the stomach, additionally comprising a step of selecting the end of said time period to be the end of the set of at least one pressure measurement.

It is another object of the present invention to disclose the method for determining the consistency of food entering the stomach, additionally comprising a step of limiting said weighting factors $g_i$ to be greater than or equal to zero and are less than or equal to one.

It is another object of the present invention to disclose the method for determining the consistency of food entering the stomach, additionally comprising a step of setting the sum of said weighting factors $g_i$ to one, g1+g2+g3=1.

It is another object of the present invention to disclose the method for determining the consistency of food entering the stomach, additionally comprising a step of setting said weighting factors $g_i$ to be equal, g1=g2=g3=⅓.

It is another object of the present invention to disclose the method for determining the consistency of food entering the stomach, additionally comprising a step of conditioning said pressure measurement data with a Butterworth low pass filter.

It is another object of the present invention to disclose the method for determining the consistency of food entering the stomach, additionally comprising a step of conditioning said pressure measurement data with a gain factor G, $$G = \frac{1}{\sqrt{1 + (2f)^4}},$$

f=½.

It is another object of the present invention to disclose the method for determining the consistency of food entering the stomach, additionally comprising a step of selecting a criterion value to carry out said distinguishing.

It is another object of the present invention to disclose the method for determining the consistency of food entering the stomach, additionally comprising a step of setting said criterion to a value greater than approximately 0.2 and less than approximately 0.4.

It is another object of the present invention to disclose the method for determining the consistency of food entering the stomach, additionally comprising a step of setting said criterion value to a value approximately 0.246.

It is another object of the present invention to disclose the method for determining the consistency of food entering the stomach, additionally comprising a step of determining said consistency of said bolus of food, wherein said bolus of food has consistency approximately the same as said bolus of said standard food if said total factor calculated assuming said food has the consistency of said standard food is greater than said criterion value.

It is another object of the present invention to disclose the method for determining the consistency of food entering the stomach, additionally comprising a step of providing an eating behavior pattern descriptive report based on the analysis of at least one eating parameter selected from a group consisting of constant speed eater, fast or accelerated speed eater, night eater, binge eater, total size of meal, average volume of meal, and average time of meal, volumetric consumption by time, shifting to liquid food consumption, vomiting events, type of food consumed, meal times during the day and duration, new adjustment validation data and short/long term change of pressure events as a result of new adjustment or any combination thereof.

It is another object of the present invention to disclose the method for determining the consistency of food entering the stomach, additionally comprising a step of providing means adapted to indicate said current eating behavior through a display to the patient.

It is another object of the present invention to disclose the method for determining the consistency of food entering the stomach, additionally comprising a step of monitoring at least one current eating behavior parameter.

It is another object of the present invention to disclose the method for determining the consistency of food entering the stomach, additionally comprising a step of calibrating said GRA to a desired restriction based on said monitored parameter.

It is another object of the present invention to disclose the method for determining the consistency of food entering the stomach, additionally comprising a step of indicating said eating behavior pattern to at least one selected from a group consisting of (a) said patient; (b) a predetermined clinician; or any combination thereof.

It is another object of the present invention to disclose the method for determining the consistency of food entering the stomach, additionally comprising a step of performing said indication by at least one selected from a group consisting of (a) said patient; (b) a predetermined clinician through appropriate instructions to said patient.

It is another object of the present invention to disclose the method for determining the consistency of food entering the stomach, additionally comprising a step of adapting said system to identify at least one of a group consisting of: what type of food is the patient consuming; how many meals does the patient have per day; is the patient chewing the food sufficiently; were there vomiting events following the calibration; after recalibrating, is the current stoma adjusted to the patient's need; what are meal durations; what are the intervals between each bite and do they correspond with the pouch emptying time; is the patient a fast eater; is the patient a night eater; what kind of food is eaten at night; does the patient drink during the meal; is there a change in the patient's pressure regime since the last calibration.

It is another object of the present invention to disclose the method for determining the consistency of food entering the stomach, additionally comprising a step of adapting said system to identify variability in said patient's eating habits.

It is another object of the present invention to disclose the method for determining the consistency of food entering the stomach, additionally comprising a step of adapting said system to warn to said patient if proper eating protocols are not being followed.

It is another object of the present invention to disclose a system for determining the consistency of food comprising:
  a. An adjustable gastric band (AGB);
  b. A pressure sensor to measure pressure within said AGB;
  c. a processing unit in communication with said pressure sensor, said processing unit containing instructions to collect at least one set of at least one pressure measurement and to analyze said at least one set of at least one pressure measurement;
  d. a data base comprising data concerning pressure exerted within said AGB by a bolus of liquid food, a bolus of semiliquid food, and a bolus of solid food;
  e. a means of recording said pressure measurements;
  f. a means of recording the results of said analysis; and
  g. a means of transmitting said results to at least one of a group consisting of a patient, a clinician, a doctor, a nurse, a dietician, and a researcher
  whereby said processing unit is adapted to provide output data distinguishing between at least two of a group consisting of liquid food, semiliquid food, and solid food.

It is another object of the present invention to disclose the system for determining the consistency of food, wherein at least one of said at least one of a group consisting of at least one of said least one set of at least one pressure measurement and said results are transmitted to a location remote from said patient.

It is another object of the present invention to disclose the system for determining the consistency of food, wherein the system can alter itself in response to changes in at least one of a group consisting of food consistency, food granularity, bolus size, and duration of eating.

It is another object of the present invention to disclose the system for determining the consistency of food, wherein said bolus of liquid food comprises a standard formulation, said bolus of semiliquid food comprises a standard formulation, and a bolus of solid food comprises a standard formulation.

It is another object of the present invention to disclose the system for determining the consistency of food, additionally comprising a database of results of analyses of a plurality of sets of at least one pressure measurement of at least one bolus of liquid food, at least one bolus of semiliquid food, and at least one bolus of solid food.

It is another object of the present invention to disclose the system for determining the consistency of food, wherein said distinction is made on the basis of a total factor, said total factor defined as Total factor $=g_1 \cdot F_{Peak} + g_2 \cdot F_{Area} + g_3 \cdot F_{Fade}$, said $g_i$ being weighting factors and said $F_i$ being local factors.

It is another object of the present invention to disclose the system for determining the consistency of food, wherein said total factor is calculated three times for each said bolus of food, once on the assumption that said food has the consistency of said liquid food, once on the assumption that said food has the consistency of said semiliquid food, and once on the assumption that said food has the consistency of said solid food.

It is another object of the present invention to disclose the system for determining the consistency of food, wherein said weighting factors $g_i$ are greater than or equal to zero and less than or equal to 1.

It is another object of the present invention to disclose the system for determining the consistency of food, wherein said local factors $F_{Peak}$, $F_{Area}$ and $F_{Fade}$ are derived from said at least one set of at least one pressure measurement.

It is another object of the present invention to disclose the system for determining the consistency of food, wherein said local factors $F_{peak}$, $F_{Area}$ and $F_{Fade}$ are greater than or equal to zero and less than or equal to 1.

It is another object of the present invention to disclose the system for determining the consistency of food, wherein said local factor $F_{Peak}$ is calculated from $$F_{Peak} = 1 - \frac{|\text{Peak} - \text{average Peak}|}{\frac{\sigma_{peak}}{2}},$$

Peak is the maximum pressure in one set of at least one pressure measurement, average Peak is the average maximum pressure of a plurality of sets of at least one pressure measurement, and $\sigma_{Peak}$ is the standard deviation of the average maximum pressure of a plurality of sets of at least one pressure measurement.

It is another object of the present invention to disclose the system for determining the consistency of food, wherein said local factor $F_{Area}$, is calculated from $$F_{Area} = 1 - \frac{|\text{Area} - \text{average Area}|}{\frac{\sigma_{Area}}{2}},$$

Area is the area under the curve of pressure vs. time generated from the at least one set of at least one pressure measurement, average Area is the average area under the curve of pressure vs. time generated from a plurality of sets of at least one pressure measurement, and $\sigma_{Area}$ is the standard deviation of the average area under the curve of pressure vs. time generated from a plurality of sets of at least one pressure measurement.

It is another object of the present invention to disclose the system for determining the consistency of food, wherein said local factor $F_{Fade}$ is calculated from $$F_{Fade} = 1 - \frac{1}{10} \frac{\sum_{j}^{i}[\text{Pressure} - \text{average Pressure}]}{j - i},$$

Pressure is pressure measurement at a time during the measurement of the at least one set of at least one pressure measurement, average Pressure is the average of pressure measurements at that time generated from a plurality of sets of at least one pressure measurement, j is the start time for the time period, and i is the end time for the time period It is another object of the present invention to disclose the system for determining the consistency of food, wherein the start of said time period occurs after the time at which the peak pressure occurs.

It is another object of the present invention to disclose the system for determining the consistency of food, wherein the start of said time period occurs after the time at which there is a minimum in the rate of change of pressure as a function of time.

It is another object of the present invention to disclose the system for determining the consistency of food, wherein the start of said time period occurs at a special point.

It is another object of the present invention to disclose the system for determining the consistency of food, wherein said special point is the intersection of the lines defining the slopes of two regions of approximately constant slope in the plot of rate of change of pressure as a function of time, said regions being after the minimum of the plot of rate of change of pressure as a function of time, said approximately constant slopes different from each other.

It is another object of the present invention to disclose the system for determining the consistency of food, wherein the end of said time period is the end of the set of at least one pressure measurement.

It is another object of the present invention to disclose the system for determining the consistency of food, wherein said weighting factors gi are greater than or equal to zero and are less than or equal to one.

It is another object of the present invention to disclose the system for determining the consistency of food, wherein the sum of said weighting factors $g_i$ is one, $g_1+g_2+g_3=1$.

It is another object of the present invention to disclose the system for determining the consistency of food, wherein said weighting factors $g_i$ are all equal, $g_1=g_2=g_3=\frac{1}{3}$.

It is another object of the present invention to disclose the system for determining the consistency of food, wherein said pressure measurement data are conditioned with a Butterworth low pass filter.

It is another object of the present invention to disclose the system for determining the consistency of food, wherein said pressure measurement data are conditioned with a gain factor G, $$G = \frac{1}{\sqrt{1 + (2f)^4}},$$

$f=\frac{1}{2}$.

It is another object of the present invention to disclose the system for determining the consistency of food, wherein said distinguishing is carried out by means of a criterion value.

It is another object of the present invention to disclose the system for determining the consistency of food, wherein said criterion value is greater than approximately 0.2 and less than approximately 0.4.

It is another object of the present invention to disclose the system for determining the consistency of food, wherein said criterion value is approximately 0.246.

It is another object of the present invention to disclose the system for determining the consistency of food, wherein said bolus of food has consistency approximately the same as said bolus of said standard food if the total factor calculated assuming said food has the consistency of said standard food is greater than said criterion value.

It is another object of the present invention to disclose the system for determining the consistency of food, wherein an eating behavior pattern descriptive report is provided based on the analysis of at least one current eating behavior parameter selected from a group consisting of constant speed eater, fast or accelerated speed eater, night eater, binge eater, total size of meal, average volume of meal, and average time of meal, volumetric consumption by time, shifting to liquid food consumption, vomiting events, type of food consumed, meal times during the day and duration, new adjustment validation data and short/long term change of pressure events as a result of new adjustment or any combination thereof.

It is another object of the present invention to disclose the system for determining the consistency of food, additionally comprising means to indicate said current eating behavior through a display to the patient.

It is another object of the present invention to disclose the system for determining the consistency of food, additionally comprising means to monitor at least one current eating behavior parameter.

It is another object of the present invention to disclose the system for determining the consistency of food, wherein said GRA is calibrated to a desired restriction based on said monitored parameter.

It is another object of the present invention to disclose the system for determining the consistency of food, additionally comprising means adapted to indicate said eating behavior pattern to at least one selected from a group consisting of (a) said patient; (b) a predetermined physician; or any combination thereof.

It is another object of the present invention to disclose the system for determining the consistency of food, wherein said indication is performed by at least one selected from a group consisting of (a) the patient; (b) said physician through appropriate instructions to said patient.

It is another object of the present invention to disclose the system for determining the consistency of food, wherein said system can identify at least one of a group consisting of what type of food is the patient consuming; how many meals does the patient have per day; is the patient chewing the food sufficiently; were there vomiting events following the calibration; after recalibrating, is the current stoma adjusted to the patient's need; what are meal durations; what are the intervals between each bite and do they correspond with the pouch emptying time; is the patient a fast eater; is the patient a night eater; what kind of food is eaten at night; does the patient drink during the meal; is there a change in the patient's pressure regime since the last calibration.

It is another object of the present invention to disclose the system for determining the consistency of food, wherein said system can identify variability in the patient's eating habits.

It is another object of the present invention to disclose the system for determining the consistency of food, wherein the system comprises a warning to the patient if proper eating protocols are not being followed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method for modifying an eating behavior of a patient equipped with a gastric restriction apparatus (GRA) comprising steps of:
  a. providing an adjustable gastric band (AGB);
  b. providing at least one pressure sensor to measure pressure within said AGB;
  c. providing a processing unit in communication with said at least one pressure sensor, said processing unit containing instructions to collect at least one set of at least one pressure measurement and to analyze said at least one set of at least one pressure measurement;
  d. providing at least one database comprising at least one set of standard data, each said at least one set of standard data derivable from pressure exerted within said AGB by a bolus of a standard food, said standard food selected from a standard food group consisting of liquid food, semiliquid food, and solid food;
  e. placing said AGB in position, said AGB at least partially surrounding a stoma near an upper end of a stomach;
  f. measuring a set of at least one said pressure within said AGB as at least one bolus of food passes through said stoma;
  g. storing said at least one set of at least one measured pressure;
  h. analyzing said at least one set of at least one measured pressure, said analysis using said at least one set of standard data, said analysis identifying an eating behavior of said patient;
  i. identifying, from said eating behavior, an eating pattern;
  j. performing at least one comparison step selected from a group consisting of: comparing said eating behavior to at least one predetermined eating behavior, comparing said eating pattern to at least one predetermined eating pattern; and
  k. providing said processing unit with instructions configured to compare, for each said at least one bolus of food, a total factor to a predetermined criterion, said total factor determinable from a member of a group consisting of maximum pressure for at least one bolus of food, area under a curve of pressure vs time for at least one bolus of food, and at least one pressure measured during passage of at least one bolus of food and after said maximum pressure, said comparison identifying a food type, said food type selected from a group consisting of liquid food, semiliquid food, and solid food,
  said method additionally comprising a step of altering pressure in said AGB in response to at least one change in the food type.

2. The method of claim 1, additionally comprising a step of transmitting at least one member of a group consisting of: said total factor and said food type to at least one member of a group consisting of a patient, a clinician, a doctor, a nurse, a dietician, and a researcher.

3. The method of claim 1, additionally comprising a step of providing instructions configured to calculate said total factor from Total factor=$g_1 \cdot F_{Peak} + g_2 \cdot F_{Area} + g_3 \cdot F_{Fade}$, said $g_i$ being weighting factors and said $F_i$ being local factors derived from said at least one set of at least one pressure measurement, wherein said local factor $F_{peak}$ is calculated from $$F_{Peak} = 1 - \frac{|\text{Peak} - \text{average Peak}|}{\frac{\sigma_{peak}}{2}},$$

wherein Peak is a maximum pressure in one set of at least one pressure measurement, average Peak is an average maximum pressure of a plurality of sets of at least one pressure measurement, and $\sigma_{Peak}$ is a standard deviation of an average maximum pressure of a plurality of sets of at least one pressure measurement; wherein said local factor $F_{Area}$ is calculated from $$F_{Area} = 1 - \frac{|\text{Area} - \text{average Area}|}{\frac{\sigma_{Area}}{2}},$$

wherein Area is the area under a curve of pressure vs. time generated from said at least one set of at least one pressure measurement, average Area is an average area under a curve of pressure vs. time generated from a plurality of sets of at least one pressure measurement, and $\sigma_{Area}$ is standard deviation of average area under a curve of pressure vs. time generated from a plurality of sets of at least one pressure measurement; and wherein said local factor $F_{Fade}$ is calculated from $$F_{Fade} = 1 - \frac{1}{10} \frac{\sum_j^i [\text{Pressure} - \text{average Pressure}]}{j-i},$$

wherein Pressure is a pressure measurement at a time during measurement of said at least one set of at least one pressure measurement, average Pressure is an average of pressure measurements at that time generated from a plurality of sets of at least one pressure measurement, j is an end time for said time period, and i is a start time for said time period.

4. The method of claim 3, additionally comprising a step of calculating said total factor a plurality of times for each said bolus of food, each said calculation of said total factor selected from a group consisting of: on an assumption that said food has a consistency of said liquid food, on an assumption that said food has a consistency of said semiliquid food, on an assumption that said food has a consistency of said solid food and any combination thereof.

5. The method of claim 3, additionally comprising a step of selecting said start time of said time period from a group consisting of: after a time at which said maximum pressure occurs; after a time at which there is a minimum in a rate of change of pressure as a function of time; and at a special point, said special point being an intersection of lines defining slopes of two regions of approximately constant slope in a plot of rate of change of pressure as a function of time, said regions being after a minimum of a plot of rate of change of pressure as a function of time, wherein said approximately constant slopes are different from each other.

6. The method of claim 1, additionally comprising a step of conditioning said at least one set of at least one measured pressure with a low pass filter.

7. The method of claim 1, additionally comprising steps of, for at least one bolus of food, selecting one member of said standard food group; calculating a total factor for said at least one bolus of food from a set of standard data for said one member of said standard food group and from said at least one set of at least one measured pressure for said at least one bolus of food; comparing said total factor to said predetermined criterion; and, said total factor being greater than said predetermined criterion, determining said at least one bolus of food to have a consistency approximately same as said one member of said standard food group.

8. The method of claim 1, additionally comprising at least one step selected from a group consisting of (a) providing an eating behavior pattern descriptive report based on an analysis of at least one eating behavior parameter selected from a group consisting of constant speed eater, fast or accelerated speed eater, night eater, binge eater, total size of meal, average volume of meal, and average time of meal, volumetric consumption by time, shifting to liquid food consumption, vomiting events, type of food consumed, meal times during the day and duration, new adjustment validation data, short term change of pressure events as a result of new adjustment, long term change of pressure events as a result of new adjustment, and any combination thereof; (b) performing at least one selected from a group consisting of: alter at least one of a group consisting of: said predetermined criterion, stored average bolus size, stored pressure behavior for a standard meal, and calibration in response to at least one change in at least one of a group consisting of food consistency, food granularity, bolus size, and duration of eating; indicate said eating behavior to said patient; indicate said eating behavior to a predetermined clinician; monitor said at least one eating behavior parameter; instruct said patient to create smaller boluses; instruct said patient to chew more thoroughly; instruct said patient to eat more slowly; warn said patient if proper eating protocols are not being followed; identify variability in eating habits of said patient; and any combination thereof.

9. The method of claim 1, additionally comprising a step of identifying at least one of a group consisting of: what type of food is being consumed; how many meals are eaten per day; if said food is being sufficiently chewed; if there were there vomiting events following a calibration; after recalibration, if said AGB is adjusted to said patient's need; what meal durations are; intervals between successive bites; said intervals correspond with pouch emptying time; if said patient is a fast eater; if said patient is a night eater; what kind of food is eaten at night; if said patient drinks during a meal; if there is a change in a pressure regime since a most recent calibration.

10. The method of claim 1, additionally comprising steps of selecting said eating pattern and said at least one predetermined eating pattern from a group consisting of: constant speed eater, fast eater, accelerated speed eater, night eater, binge eater, and any combination thereof; and selecting said eating behavior and said predetermined eating behavior from a group consisting of: total size of meal, average volume of meal, average time of meal, volumetric consumption by time, shifting to liquid food consumption, vomiting events, type of food consumed, meal times during a day, meal duration, and any combination thereof.

11. The method of claim 1, additionally comprising a step of providing, based on said at least one comparison step, at least one instruction, said at least one instruction configured to modify said eating behavior of said patient.

12. A system for modifying an eating behavior of a patient equipped with a gastric restriction apparatus comprising:
   a. at least one adjustable gastric band (AGB);
   b. at least one pressure sensor to measure pressure within said AGB;
   c. at least one processing unit in communication with said at least one pressure sensor, said processing unit containing instructions to collect, for at least one bolus of food, at least one set of at least one pressure measurement, to analyze said at least one set of at least one pressure measurement, said analysis using at least one set of standard data, said analysis configured to identify said eating behavior of said patient; by comparison of said eating behavior to at least one predetermined eating behavior, determining at least one modification to said eating behavior of said patient;
   d. at least one database comprising said at least one set of standard data, each of said at least one set of standard data derivable from pressure exerted within said AGB by a bolus of a standard food, said standard food selected from a standard food group consisting of liquid food, semiliquid food, and solid food;
   e. at least one database configured to store said at least one set of at least one measured pressure; and
   f. at least one database configured to store results of at least one said analysis of said at least one set of at least one measured pressure; wherein said analysis additionally comprises instructions configured to compare, for each said at least one bolus of food, a total factor to a predetermined criterion, said total factor determinable from a member of a group consisting of maximum pressure for at least one bolus of food, area under a curve of pressure vs time for at least one bolus of food, and at least one pressure measured during passage of at least one bolus of food and after said maximum pressure, said comparison identifying a food type, said food type selected from a group consisting of liquid food, semiliquid food, and solid food, further wherein said system is configured to alter pressure in said AGB in response to at least one change in the food type.

13. The system of claim 12, wherein said results are communicable to at least one of a group consisting of a patient, a clinician, a doctor, a nurse, a dietician, and a researcher.

14. The system of claim 12, wherein said processing unit additionally comprises instructions to calculate said total factor from Total factor=$g_1 \cdot F_{Peak} + g_2 \cdot F_{Area} + g_3 \cdot F_{Fade}$, said $g_i$ being weighting factors and said $F_i$ being local factors derived from said at least one set of at least one pressure measurement, wherein said local factor $F_{peak}$ is calculated from $$F_{Peak} = 1 - \frac{|\text{Peak} - \text{average Peak}|}{\frac{\sigma_{peak}}{2}},$$

wherein Peak is a maximum pressure in one set of at least one pressure measurement, average Peak is an average maximum pressure of a plurality of sets of at least one pressure measurement, and $\sigma_{Peak}$ is a standard deviation of the average maximum pressure of a plurality of sets of at least one pressure measurement; wherein said local factor $F_{Area}$ is calculated from $$F_{Area} = 1 - \frac{|\text{Area} - \text{average Area}|}{\frac{\sigma_{Area}}{2}},$$

wherein Area is the area under a curve of pressure vs. time generated from said at least one set of at least one pressure measurement, average Area is an average area under a curve of pressure vs. time generated from a plurality of sets of at least one pressure measurement, and $\sigma_{Area}$ is a standard deviation of an average area under a curve of pressure vs. time generated from a plurality of sets of at least one pressure measurement; and wherein said local factor $F_{Fade}$ is calculated from $$F_{Fade} = 1 - \frac{1}{10} \frac{\sum_{j}^{i} [\text{Pressure} - \text{average Pressure}]}{j - i},$$

wherein Pressure is a pressure measurement at any time during measurement of said at least one set of at least one pressure measurement, average Pressure is an average of pressure measurements at that time generated from a plurality of sets of at least one pressure measurement, j is an end time for a time period, and i is a start time for said time period.

15. The system of claim 14, wherein said instructions include instructions to calculate said total factor a plurality of times for each said bolus of food, said instructions selected from a group consisting of: calculate said total factor on an assumption that said food has a consistency of said liquid food, calculate said total factor on an assumption that said food has a consistency of said semiliquid food, calculate said total factor on an assumption that said food has a consistency of said solid food and any combination thereof.

16. The system of claim 15, wherein said start time is selected from a group consisting of: after a time at which said maximum pressure occurs; after a time at which there is a minimum in a rate of change of pressure as a function of time; and at a special point, said special point being an intersection of lines defining slopes of two regions of approximately constant slope in a plot of rate of change of pressure as a function of time, said regions being after a minimum of a plot of rate of change of pressure as a function of time, wherein said approximately constant slopes are different from each other.

17. The system of claim 12, wherein said processing unit contains instructions configured to condition said at least one set of at least one pressure measurement with a low pass filter.

18. The system of claim 12, wherein said processing unit contains instructions configured to perform the following: for at least one bolus of food, select one member from said standard food group; calculate a total factor for said at least one bolus of food from a set of standard data for said one member of said standard food group and from said at least one set of at least one measured pressure for said at least one bolus of food; compare said total factor to said predetermined criterion, and, for said total factor being greater than said predetermined criterion, determine said bolus of food to have a consistency approximately the same as said one member of said standard food group.

19. The system of claim 18, wherein said predetermined criterion is approximately 0.246 on a scale with a range from 0 to 1, said scale with a range from 0 to 1 being a scale of said total factor.

20. The system of claim 12, wherein an eating behavior pattern descriptive report is provided based on an analysis of at least one eating behavior parameter selected from a group consisting of; constant speed eater, fast or accelerated speed eater, night eater, binge eater, total size of meal, average volume of meal, average duration of meal, volumetric consumption by time, shifting to liquid food consumption, vomiting events, type of food consumed, meal times during a day, new adjustment validation data, short term change of pressure events as a result of new adjustment, long term change of pressure events as a result of new adjustment, and any combination thereof.

21. The system of claim 20, wherein said processing unit contains instructions configured to perform at least one step selected from a group consisting of: alter at least one of: said predetermined criterion, stored average bolus size, stored pressure behavior for a standard meal, and calibration in response to at least one change in at least one of a group consisting of food consistency, food granularity, bolus size, and duration of eating; indicate said eating behavior to said patient; indicate said eating behavior to a predetermined clinician; monitor at least one said eating behavior parameter; instruct said patient to create smaller boluses; instruct said patient to chew more thoroughly; instruct said patient to eat more slowly; warn said patient if proper eating protocols are not being followed; and identify variability in eating habits of said patient.

22. The system of claim 12, wherein said system is configured to identify at least one of a group consisting of: what type of food is being consumed; how many meals are eaten per day; if said food is being sufficiently chewed; if there were vomiting events following a calibration; after recalibration, if said AGB is adjusted to a need of said patien; what meal durations are; intervals between successive bites; if said intervals correspond with pouch emptying time; if the patient is a fast eater; if the patient is a night eater; what kind of food is eaten at night; if the patient drinks during the meal; if there is a change in pressure regime since a most recent calibration.

\* \* \* \* \*